US009861558B2

(12) United States Patent
Lynch et al.

(10) Patent No.: US 9,861,558 B2
(45) Date of Patent: *Jan. 9, 2018

(54) METHODS OF FORMING AN AQUEOUS TREATMENT LIQUOR BY DISSOLVING A POROUS SOLID WITH A BENEFIT AGENT COATING

(71) Applicant: The Procter & Gamble Company, Cincinnati, OH (US)

(72) Inventors: Matthew Lawrence Lynch, Mariemont, OH (US); Robert Wayne Glenn, Jr., Liberty Township, OH (US); Joanne Roberta Willman, Fairfield, OH (US); Benjamin John Kutay, Cincinnati, OH (US); Philip Andrew Sawin, Cincinnati, OH (US); Mark William Hamersky, Hamilton, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/702,789

(22) Filed: May 4, 2015

(65) Prior Publication Data

US 2015/0313806 A1 Nov. 5, 2015

Related U.S. Application Data

(60) Provisional application No. 61/988,640, filed on May 5, 2014.

(51) Int. Cl.
*A61Q 5/02* (2006.01)
*A61Q 5/12* (2006.01)
*C11D 1/82* (2006.01)
*C11D 9/36* (2006.01)
*A61K 8/04* (2006.01)
*A61K 8/89* (2006.01)
*A61K 8/34* (2006.01)
*A61K 8/81* (2006.01)
*A61K 8/891* (2006.01)
*A61K 8/898* (2006.01)
*A61K 8/02* (2006.01)

(52) U.S. Cl.
CPC ............ *A61K 8/046* (2013.01); *A61K 8/0216* (2013.01); *A61K 8/345* (2013.01); *A61K 8/8129* (2013.01); *A61K 8/89* (2013.01); *A61K 8/891* (2013.01); *A61K 8/898* (2013.01); *A61Q 5/02* (2013.01); *A61Q 5/12* (2013.01)

(58) Field of Classification Search
CPC ... A61Q 5/02; A61Q 5/12; C11D 1/82; C11D 3/162; C11D 3/373; C11D 3/3753; C11D 9/225; C11D 9/36; C11D 17/042
See application file for complete search history.

(56) References Cited

U.S. PATENT DOCUMENTS

| | | | |
|---|---|---|---|
| 5,098,636 A | 3/1992 | Balk | |
| 6,187,728 B1* | 2/2001 | McManus | A47K 7/03 510/142 |
| 6,382,526 B1 | 7/2002 | Reneker et al. | |
| 6,451,750 B2* | 9/2002 | Hewitt | C11D 17/043 510/296 |
| 7,291,300 B2 | 6/2007 | Chhabra et al. | |
| 2010/0254961 A1* | 10/2010 | Nishio | A61K 8/0208 424/94.1 |
| 2010/0291165 A1* | 11/2010 | Glenn, Jr. | A61K 8/046 424/401 |
| 2011/0182956 A1* | 7/2011 | Glenn, Jr. | A61K 8/0216 424/401 |
| 2011/0189247 A1* | 8/2011 | Glenn, Jr. | A61K 8/0216 424/401 |
| 2012/0289451 A1* | 11/2012 | Glenn, Jr. | A61K 8/11 512/4 |
| 2013/0303419 A1* | 11/2013 | Glenn, Jr. | A61K 8/046 510/120 |
| 2015/0313803 A1 | 11/2015 | Lynch et al. | |
| 2015/0313804 A1 | 11/2015 | Lynch et al. | |
| 2015/0313805 A1 | 11/2015 | Lynch et al. | |
| 2015/0313806 A1 | 11/2015 | Lynch et al. | |
| 2015/0313807 A1 | 11/2015 | Lynch et al. | |
| 2015/0313808 A1 | 11/2015 | Lynch et al. | |
| 2015/0313809 A1 | 11/2015 | Lynch et al. | |
| 2016/0271021 A1 | 9/2016 | Glenn, Jr. | |

FOREIGN PATENT DOCUMENTS

EP 0094959 7/1987
GB 2365440 A 2/2002
(Continued)

OTHER PUBLICATIONS

U.S. Appl. No. 14/702,787, filed May 4, 2015, Matthew Lawrence Lynch et al.
U.S. Appl. No. 14/702,788, filed May 4, 2015, Matthew Lawrence Lynch et al.
U.S. Appl. No. 14/702,789, filed May 4, 2015, Matthew Lawrence Lynch et al.
U.S. Appl. No. 14/702,790, filed May 4, 2015, Matthew Lawrence Lynch et al.

(Continued)

*Primary Examiner* — Charles Boyer
(74) *Attorney, Agent, or Firm* — Jason J Camp

(57) ABSTRACT

A method of forming an aqueous treatment liquor comprising a benefit agent, the method comprising the steps of: (a) providing a consumer product comprising: (i) a porous dissolvable solid structure, and (ii) a hydrophobic coating comprising a benefit agent, the hydrophobic coating applied to the porous dissolvable solid structure, wherein the hydrophobic coating has a first viscosity; (b) providing an aqueous solution; and (c) dissolving the consumer product in the aqueous solution to form an aqueous treatment liquor comprising a hydrophobic portion and an aqueous portion, wherein the aqueous portion has a second viscosity. A ratio of the first viscosity of the hydrophobic coating to the second viscosity of the aqueous portion of the aqueous treatment liquor is less than about 100:1.

17 Claims, 2 Drawing Sheets

(56) References Cited

FOREIGN PATENT DOCUMENTS

| WO | WO200154667 A1 | 2/2001 |
|----|----------------|--------|
| WO | WO200922761 A1 | 2/2009 |
| WO | WO 2009095891 | 8/2009 |
| WO | WO2012003349 | 1/2012 |

OTHER PUBLICATIONS

U.S. Appl. No. 14/702,792, filed May 4, 2015, Matthew Lawrence Lynch et al.
U.S. Appl. No. 14/702,793, filed May 4, 2015, Matthew Lawrence Lynch et al.
U.S. Appl. No. 15/374,486, filed Feb. 9, 2016, Glenn, Jr. et al.
Anonymous: "Chocolate-coated marshmallow treats—Wikipedia, the free encyclopedia", Jan. 1, 1800, XP055198552, URL:https://en.wikipedia.org/wiki/Chocolate-coated_marshmallow_treats.
International Search Report and Written Opinion dated Jun. 30, 2015, 14 pgs.
International Search Report and Written Opinion dated Jul. 6, 2015, 17 pgs.
International Search Report and Written Opinion dated Jul. 9, 2015, 14 pgs.
International Search Report and Written Opinion dated Jul. 6, 2015, 15 pgs.

* cited by examiner

US 9,861,558 B2

METHODS OF FORMING AN AQUEOUS TREATMENT LIQUOR BY DISSOLVING A POROUS SOLID WITH A BENEFIT AGENT COATING

FIELD OF THE INVENTION

The present invention relates to a method of forming an aqueous treatment liquor comprising dissolving, in an aqueous solution, a consumer product comprising a porous dissolvable solid structure and a hydrophobic coating applied thereto.

BACKGROUND OF THE INVENTION

Consumer products often contain benefit agents, such as conditioning agents or perfume, to provide enhancements to surfaces treated with the consumer product such as improved hand feel benefits (e.g. soft, silky feel), odor control benefits, and the like. Such benefits are desired by consumers of products such as hair care products, like shampoo or hair conditioners, and fabric care products, such as laundry detergents or fabric softeners.

Such consumer products are typically provided in the form of aqueous liquid products. Since many desirable benefit agents are hydrophobic in nature, it can be a challenge to create a stable aqueous liquid formulation containing hydrophobic benefit agents. As a result, such benefit agents are typically incorporated in aqueous liquid compositions in the form of emulsions or other systems comprising emulsion droplets/particles having relatively small particle size benefits agents. One drawback of having small particle size benefit agents is that it can be difficult to deposit and retain small particle size benefit agents on the treated surface, especially if the surfaces are being treated in the context of an aqueous treatment liquor such as a detergent treatment liquor in a washing machine or a treatment liquor that a consumer uses in the shower when shampooing and/or conditioning her hair. As a result, the small particle size benefit agents can be easily washed down the drain and therefore wasted, as opposed to being deposited and retained on surfaces to enhance the surface.

Past attempts to enhance deposition of relatively small particle size benefits agents have generally relied on the use of deposition aids and/or coacervates, such as cationic polymers and/or complexes formed between deposition aids and other ingredients in the treatment liquor. This approach suffers from a disadvantage in that such deposition aids and/or coacervates may be undesirable on the treated surface, may increase cost or complexity of the consumer product, or may create other issues such as material incompatibilities.

In order to address such drawbacks, attempts have been made to provide delivery systems, such as encapsulation systems, for the hydrophobic benefit agents in order to enhance their deposition and retention on surfaces while remaining stable in an aqueous liquid product. These delivery systems, however, can limit the effectiveness of the benefit agents or lead to other issues.

It is therefore desired to provide a consumer product that can provide an aqueous treatment liquor having relatively large particle size benefit agents without the need for liquid delivery systems that can interfere with the effectiveness of the benefit agent being deposited on the treated surfaces.

SUMMARY OF THE INVENTION

The present invention relates to a method of forming an aqueous treatment liquor comprising a benefit agent, the method comprising the steps of: (a) providing a consumer product comprising: (i) a porous dissolvable solid structure, and (ii) a hydrophobic coating comprising a benefit agent, the hydrophobic coating applied to the porous dissolvable solid structure, wherein the hydrophobic coating has a first viscosity; (b) providing an aqueous solution; and (c) dissolving the consumer product in the aqueous solution to form an aqueous treatment liquor comprising a hydrophobic portion and an aqueous portion, wherein the aqueous portion has a second viscosity. A ratio of the first viscosity of the hydrophobic coating to the second viscosity of the aqueous portion of the aqueous treatment liquor is less than about 100:1.

The method therefore relates to dissolving a consumer product in an aqueous solution to form an aqueous treatment liquor. Upon dissolution, the hydrophobic coating can be transformed from a liquid film coating into large discrete particles by action on (via dissolution and/or shear) the solid structure supporting the hydrophobic coating dissolving in the aqueous solution. The relatively large particles of benefit agent can be more effectively deposited on the treated surfaces and therefore provide enhanced consumer benefits, as compared to products which provide smaller particle size benefit agents.

DETAILED DESCRIPTION OF THE INVENTION

Figure 1A:
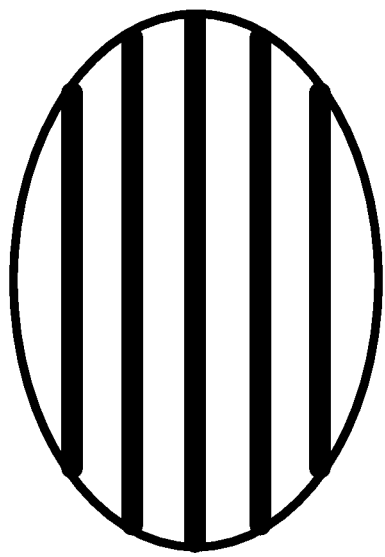
FIGS. 1A and 1B are top views of consumer products of the present invention.

The present invention relates to a method of forming an aqueous treatment liquor comprising a benefit agent, the method comprising the steps of: (a) providing a consumer product comprising: (i) a porous dissolvable solid structure, and (ii) a hydrophobic coating comprising a benefit agent, the hydrophobic coating applied to the porous dissolvable solid structure, wherein the hydrophobic coating has a first viscosity; (b) providing an aqueous solution; and (c) dissolving the consumer product in the aqueous solution to form an aqueous treatment liquor comprising a hydrophobic portion and an aqueous portion, wherein the aqueous portion has a second viscosity. A ratio of the first viscosity of the hydrophobic coating to the second viscosity of the aqueous portion of the aqueous treatment liquor is less than about 100:1.

As used herein, consumer product compositions encompass beauty care compositions, fabric and home care compositions, and health care compositions. Beauty care compositions generally include compositions for treating hair, including, bleaching, coloring, dyeing, conditioning, growing, removing, retarding growth, shampooing, styling; deodorants and antiperspirants; personal cleansing; color cosmetics; products, and/or methods relating to treating skin, including application of creams, lotions, and other topically applied products for consumer use; and products and/or methods relating to orally administered materials for enhancing the appearance of hair, skin, and/or nails ; and shaving. Fabric and home care compositions generally include compositions for treating fabrics, hard surfaces and any other surfaces in the area of fabric and home care, such as car care, dishwashing, fabric conditioning (including softening), laundry detergency, laundry and rinse additive and/or care, hard surface cleaning and/or treatment, and other cleaning for consumer or institutional use. Oral care compositions generally include compositions for use with any soft and/or hard tissue of the oral cavity or conditions associated therewith, e.g., anti-caries compositions, anti-microbial compositions, anti-plaque chewing gum, compositions, breath compositions, confectionaries, dentifrices/toothpastes, denture compositions, lozenges, rinses, and tooth whitening compositions. Other potential consumer products include over-the-counter or pharmaceutical medicaments, or products for treatment of mucosal tissue.

Suitable consumer products are selected from the group consisting of beauty care products, hand washing products, body wash products, shampoo products, conditioner products, cosmetic products, hair removal products, laundry products, laundry rinse additive products, laundry detergent products, hard surface cleaning products, hand dishwashing products, automatic dishwashing products, and unit dose form automatic dishwashing or laundry products.

Porous Dissolvable Solid Structure

The porous dissolvable solid structure of the present invention is intended to serve as a support structure for the hydrophobic coating. The porous dissolvable solid structure is capable of dissolving in aqueous solution to form an aqueous treatment liquor. The dissolution of the porous dissolvable solid structure facilitates break-up of the hydrophobic coating and thereby form relatively large particles of benefit agent, which can more effectively deposit and remain on surfaces treated with the aqueous treatment liquor.

The porous dissolvable solid structure of the present invention can comprise components selected from the group consisting of surfactants, water-soluble polymer structurants, plasticizers, rheology modifiers, other optional ingredients, and mixtures thereof.

Surfactants

The porous dissolvable solid structures of the present invention may be lathering or non-lathering under consumer relevant usage instructions. The porous dissolvable structures may include at least one surfactant as a processing aid. The surfactant may also serve other functions as a foaming and/or cleansing agent.

Lathering porous dissolvable solid structures for the purposes of lathering and/or cleaning comprise from about 10% to about 75%, in one aspect from about 30% to about 70%, and in another aspect from about 40% to about 65% by weight of the consumer product of surfactant; wherein the surfactant comprises one or more surfactants from Group I, wherein Group I includes anionic surfactants which are suitable for use in hair care or other personal care compositions, and optionally one or more surfactants from Group II, wherein Group II includes a surfactant selected from the group consisting of amphoteric, zwitterionic and combinations thereof suitable for use in hair care or other personal care compositions; wherein the ratio of Group I to Group II surfactants is from about 100:0 to about 30:70. In another aspect of the present invention the ratio of Group I to Group II surfactants is from about 85:15 to about 40:60. In yet another aspect of the present invention the ratio of Group I to Group II surfactants is from about 70:30 to about 55:45.

Non limiting examples of anionic surfactants are described in U.S. Pat. Nos. 2,486,921; 2,486,922; and 2,396,278. The anionic surfactant can be selected from the group consisting of alkyl and alkyl ether sulfates, sulfated monoglycerides, sulfonated olefins, alkyl aryl sulfonates, primary or secondary alkane sulfonates, alkyl sulfosuccinates, acid taurates, acid isethionates, alkyl glycerylether sulfonate, sulfonated methyl esters, sulfonated fatty acids, alkyl phosphates, acyl glutamates, acyl sarcosinates, alkyl lactylates, anionic fluorosurfactants, sodium lauroyl glutamate, and combinations thereof.

Non limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Additional suitable Group I and Group II surfactants include those disclosed in U.S. Patent Application No. 61/120,765 and those surfactants disclosed in McCutcheon's Detergents and Emulsifiers, North American Edition (1986), Allured Publishing Corp.; McCutcheon's, Functional Materials, North American Edition (1992), Allured Publishing Corp.; and U.S. Pat. No. 3,929,678 (Laughlin et al.). Other non-limiting examples of suitable surfactants are included in U.S. Ser. No. 61/120,790. In another aspect, the porous dissolvable solid structure of the present invention can also take the form of a dissolvable fibrous web structure.

The non-lathering porous dissolvable solid structures comprise from about 10% to about 75%, in another aspect from about 15% to about 60%, and in another aspect from about 20% to about 50% by weight of the consumer product of surfactant; wherein the surfactant comprises one or more of the surfactants described below.

Anionic Surfactants

If the porous dissolvable solid structure of the present invention is non lathering, the structure may comprise a maximum level of 10% (or less than 10%) of anionic surfactants to be used primarily as a process aid in making a stable foam solid.

Cationic Surfactants

In one aspect cationic surfactants are included as a process aid in making a stable porous dissolvable solid structure. Suitable cationic surfactants for use in the present invention include those described in McCutcheon's Detergents and Emulsifiers, North American edition (1986), Allured Publishing Corp., and McCutcheon's Functional Materials, North American edition (1992). Suitable quaternary ammonium cationic conditioner actives can include cetyltrimethylammonium chloride, behenyltrimethylammonium chloride (BTAC), stearyltrimethylammonium chloride, cetylpyridinium chloride, octadecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, distearyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate.

In a particular aspect, the quaternary ammonium cationic conditioner actives for use in the invention are cetyltrimethylammonium chloride, available commercially, for example as GENAMIN CTAC by Clariant and Arquad 16/29 supplied by Akzo Nobel, behenyltrimethylammonium chloride (BTMAC) such as GENAMIN KDMP supplied by Clariant, and distearyldimethylammonium chloride such as GENAMIN DSAP supplied by Clariant. Mixtures of any of the foregoing materials may also be suitable. In a preferred aspect, the quaternary ammonium cationic conditioner active is behenyltrimethylammonium chloride (BTMAC).

Non-Ionic Surfactants

In one aspect non-ionic surfactants are included as a process aid in making a stable porous dissolvable solid structure. Suitable nonionic surfactants for use in the present invention include those described in McCutcheon's Detergents and Emulsifiers, North American edition (1986), Allured Publishing Corp., and McCutcheon's Functional Materials, North American edition (1992). Suitable nonionic surfactants for use in the personal care compositions of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

Polymeric Surfactants

Polymeric surfactants can also be surfactants to be employed as a process aid in making the porous dissolvable solid structure of the present invention, either alone or in combination with ionic and/or nonionic surfactants. Suitable polymeric surfactants for use in the personal care compositions of the present invention include, but are not limited to, block copolymers of ethylene oxide and fatty alkyl residues, block copolymers of ethylene oxide and propylene oxide, hydrophobic ally modified polyacrylates, hydrophobically modified celluloses, silicone polyethers, silicone copolyol esters, diquaternary polydimethylsiloxanes, and co-modified amino/polyether silicones.

Water-Soluble Polymer Structurant

The porous dissolvable solid structure may comprise at least one water-soluble polymer that functions as a structurant. As used herein, the term "water-soluble polymer" is broad enough to include both water-soluble and water-dispersible polymers, and is defined as a polymer with a solubility in water, measured at 25° C., of at least about 0.1 gram/liter (g/L). In some aspects, the polymers have solubility in water, measured at 25° C., of from about 0.1 gram/liter (g/L) to about 500 grams/liter (g/L). (This indicates production of a macroscopically isotropic or transparent, colored or colorless solution). The polymers for making these solids may be of synthetic or natural origin and may be modified by means of chemical reactions. They may or may not be film-forming If the surface to be treated is a physiological surface, such as hair or skin, these polymers should be physiologically acceptable, i.e., they should be compatible with the skin, mucous membranes, the hair and the scalp.

The one or more water-soluble polymers may be present from about 10% to about 50% by weight of the porous dissolvable solid structure, in one aspect from about 15% to about 40% by weight of the porous dissolvable solid structure, and in yet another aspect from about 20% to about 30% by weight of the porous dissolvable solid structure.

The one or more water-soluble polymers of the present invention are selected such that their weighted average molecular weight is from about 40,000 to about 500,000, in one aspect from about 50,000 to about 400,000, in yet another aspect from about 60,000 to about 300,000, and in still another aspect from about 70,000 to about 200,000. The weighted average molecular weight is computed by summing the average molecular weights of each polymer raw material multiplied by their respective relative weight percentages by weight of the total weight of polymers present within the porous dissolvable solid structure.

The water-soluble polymer(s) of the present invention can include, but are not limited to, synthetic polymers as described in U.S. Ser. No. 61/120,786 including polymers derived from acrylic monomers such as the ethylenically unsaturated carboxylic monomers and ethylenically unsaturated monomers as described in U.S. Pat. No. 5,582,786 and EP-A-397410. The water-soluble polymer(s) which are suitable may also be selected from naturally sourced polymers including those of plant origin examples which are described in U.S. Ser. No. 61/120,786. Modified natural polymers are also useful as water-soluble polymer(s) in the present invention and are included in U.S. Ser. No. 61/120,786. In one aspect, water-soluble polymers of the present invention include polyvinyl alcohols, polyacrylates, polymethacrylates, copolymers of acrylic acid and methyl acrylate, polyvinylpyrrolidones, polyalkylene oxides, starch and starch derivatives, pullulan, gelatin, hydroxypropylmethylcelluloses, methycelluloses, and carboxymethycelluloses. In another aspect, water-soluble polymers of the present invention include polyvinyl alcohols, and hydroxypropylmethylcelluloses. Suitable polyvinyl alcohols include those available from Celanese Corporation (Dallas, Tex.) under the CELVOL® trade name. Suitable hydroxypropylmethylcelluloses include those available from the Dow Chemical Company (Midland, Mich.) under the METHOCEL® trade name.

Plasticizer

The porous dissolvable solid structure of the present invention may comprise a water soluble plasticizing agent suitable for use in personal care compositions. In one aspect, the one or more plasticizers may be present from about 0.1% to about 30% by weight of the porous dissolvable solid structure; in another aspect from about 3% to about 25%; in another aspect from about 5% to about 20%, and in yet another aspect, from about 8% to about 15%. Non-limiting examples of suitable plasticizing agents include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, and high fructose corn syrup solids and ascorbic acid. Suitable examples of polycarboxylic acids for use herein are disclosed in U.S. Ser. No. 61/120,786.

In one aspect, the plasticizers include glycerin or propylene glycol and combinations thereof. European Patent Number EP283165B1 discloses other suitable plasticizers, including glycerol derivatives such as propoxylated glycerol.

Rheology Modifier

The porous dissolvable solid structure may comprise a rheology modifier. The rheology modifier may be combined with the aforementioned water soluble polymeric structurants.

The weight-average molecular weight of the rheology modifier may be from about 500,000 to about 10,000,000, in one aspect from about 1,000,000 to about 8,000,000, and in another aspect from about 2,000,000 to about 6,000,000. The rheology modifier, may be present from about 0 wt % to about 5 wt %, by weight of the porous dissolvable solid structure of an rheology modifier, alternatively from about 0.1 wt % to about 4 wt %, in one aspect from about 0.25 wt % to about 3 wt %, and in another aspect from about 0.5 wt % to about 2 wt % by weight of the porous dissolvable solid structure of an rheology modifier. In such instances, the weight percentage of the rheology modifier may be less than about 10%, in another aspect less than 5%, and in yet another aspect less 2% by weight of the processing mixture forming the porous dissolvable solid structure.

In one aspect, two or more rheology modifiers of differing molecular weights may be combined in various ratios in an aspect to get a desired weight-average molecular weight and overall molecular weight distribution suitable for forming fibers, provided that each of the individually sourced polymers has a weight-average molecular weight of from about 500,000 to about 10,000,000. In an aspect, a high weight-average molecular weight polymer may be combined with a low weight-average molecular weight polymer to obtain rheological properties, such as shear viscosity, elongational viscosity, and elasticity of the processing mixture desirable for fiber formation. One ordinary skilled in the art of fiber forming may be able to optimize the ratio of the high and low weight-average molecular weight polyethylene oxide to obtain desirable rheological properties.

The rheology modifiers may be selected from polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, shellac, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; guar derivatives such as hydroxypropyl guar; and combinations thereof.

In one aspect, the rheology modifiers include polyethylene oxides. In a another aspect, an about 8,000,000 weight-average molecular weight polyethylene oxide may be combined with an about 1,000,000 weight-average molecular weight polyethylene oxide in ratios ranging from about 5:95 to about 95:5 by weight. In another aspect, an about 6,000,000 weight-average molecular weight polyethylene oxide may be combined with an about 2,000,000 weight-average molecular weight polyethylene oxide in ratios ranging from about 5:95 to about 95:5 by weight. In still another aspect, an about 10,000,000 weight-average molecular weight polyethylene oxide may be combined with an about 1,000,000 weight-average molecular weight polyethylene oxide in ratios ranging from about 1:99 to about 99:1 by weight.

Active Agents

The porous dissolvable solid structure may optionally further comprise active agents typically utilized in consumer product compositions, such as beauty care compositions, fabric care compositions, and the like, provided that such active agents are compatible with the selected materials of the porous dissolvable solid structure described herein, or do not otherwise unduly impair the performance of the porous dissolvable solid structure.

Suitable active agents for incorporation in the porous dissolvable solid structure (i.e. for incorporation into the premix or resin used to make the porous dissolvable solid structure) include personal cleansing and/or conditioning agents such as hair care agents such as shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; liquid and/or powder dishwashing agents (for hand dishwashing and/or automatic dishwashing machine applications), hard surface care agents, and/or conditioning agents and/or polishing agents; other cleaning and/or conditioning agents such as antimicrobial agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, carpet care agents, dye transfer-inhibiting agents, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, teeth whitening agents, tooth care agents, mouthwash agents, periodontal gum care agents, edible agents, dietary agents, vitamins, minerals; water-treatment agents such as water clarifying and/or water disinfecting agents, and mixtures thereof.

Suitable active agents are described in detail in US 2012/0052037 A1.

Other optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Examples of such optional ingredients are disclosed in U.S. Ser. No. 12/361,634, 10/392422 filed Mar. 18, 2003, and US Publication 2003/0215522A1, dated Nov. 20, 2003.

Other optional ingredients include organic solvents, especially water miscible solvents and co-solvents useful as solubilizing agents for polymeric structurants and as drying accelerators. Examples of suitable organic solvents are disclosed in U.S. Ser. No. 12/361,634. Other optional ingredients include: latex or emulsion polymers, thickeners such as water soluble polymers, clays, silicas, ethylene glycol distearate, deposition aids, including coacervate forming components. Additional optional ingredients include anti-dandruff actives including but not limited to zinc pyrithione, selenium sulfide and those actives disclosed in US Publication 2003/0215522A1.

Types of Porous Dissolvable Solid Structures

The porous dissolvable solid structure of the present invention can be provided in the form of a foam (preferably an open-cell foam), a fibrous structure, and the like.

The porous dissolvable solid structure is preferably not in the form of a granular structure(s).

Foam

In one aspect, the porous dissolvable solid structure can be in the form of a foam, which can be an open-cell foam, a closed-cell foam, or combinations thereof. The foam preferably comprises a surfactant, a water-soluble polymer, and a plasticizer. The porous dissolvable solid structure can be prepared such that it can be conveniently and quickly dissolved in an aqueous solution to form an aqueous treatment liquor. The aqueous treatment liquor can then be used to treat surfaces, such as hair, skin, or fabrics.

The porous dissolvable solid structure in the form of a foam can have a basis weight of from about 125 grams/m$^2$ to about 3,000 grams/m$^2$, from about 300 grams/m$^2$ to about 2,500 grams/m$^2$, from about 400 grams/m$^2$ to about 2,000 grams/m$^2$, from about 500 grams/m$^2$ to about 1,500 grams/m$^2$, from about 600 grams/m$^2$ to about 1,200 grams/m$^2$, or from about 700 to about 1,000 grams/m$^2$. The porous dissolvable solid structure in the form of a foam can have a solid density of from about 0.03 g/cm$^3$ to about 0.40 g/cm$^3$, from about 0.05 g/cm$^3$ to about 0.35 g/cm$^3$, from about 0.08 g/cm$^3$ to about 0.30 g/cm$^3$, from about 0.10 g/cm$^3$ to about 0.25 g/cm$^3$, or from about 0.12 g/cm$^3$ to about 0.20 g/cm$^3$.

Suitable porous dissolvable solid structures in the form of a foam are described in detail in US 2010/0291165 A1 and U.S. Application Ser. No. 61/982,736.

Process of Making Foam

In general, a process of making a porous dissolvable solid structure in the form of a foam, in particular an open-cell foam, comprises the steps of:
  (a) preparing a pre-mixture comprising ingredients of the porous dissolvable solid structure, such as surfactant(s), water-soluble polymer structurants, plasticizers, rheology modifiers, other optional ingredients, and not more than about 60 wt % water; wherein the pre-mixture typically:
    (i) has a viscosity at 70° C. of from about 1000 cps to about 100,000 cps; and
    (ii) is heated to a temperature in the range of from about 60° C. to about 100° C.;
  (b) aerating the pre-mixture by introducing a gas into the pre-mixture to form a wet aerated mixture, wherein said wet aerated mixture typically comprises:
    (i) a density of from about 0.15 to about 0.65 g/ml; and
    (ii) bubbles having a diameter of from about 5 to about 100 microns;
  (c) dosing the wet aerated mixture into individual cavities in a mold or as a continuous sheet; and
  (d) drying the wet aerated mixture by applying energy to heat the wet aerated mixture and evaporate water to provide a porous dissolvable solid structure.

Suitable processes for making a porous dissolvable solid structure in the form of a foam are described in detail in US 2010/0291165 A1 and U.S. application Ser. No. 61/982,736.

Fibrous Structure

In one aspect, the porous dissolvable solid structure of the present invention can also take the form of a fibrous web structure. The porous dissolvable solid structure can comprise a single fibrous web structure or multiple fibrous web structures that are optionally bonded together via a bonding means (e.g. heat, moisture, ultrasonic, pressure, and the like).

Fibrous structures as porous dissolvable solid structures of the present invention will typically have a basis weight of from about 30 g/m$^2$ to about 1,000 g/m$^2$, from about 60 g/m$^2$ to about 800 g/m$^2$, from about 90 g/m$^2$ to about 700 g/m$^2$, or from about 120 g/m$^2$ to about 650 g/m$^2$. Fibrous structures herein will typically have a thickness of from about 0.25 mm to about 10 mm, from about 0.5 mm to about 7 mm, or from about 0.75 mm to about 6 mm.

Suitable porous dissolvable solid structures in the form of fibrous web structures are described in detail in US 2012/0021026 A1, U.S. Application Ser. No. 61/982,469, and U.S. Application Ser. No. 61/982,736.

Process of Making Fibrous Structure

In general, a process of making a porous dissolvable solid structure in the form of a fibrous structure comprises the steps of:
  (a) preparing a processing mixture comprising ingredients of the porous dissolvable solid structure, such as surfactant(s), water-soluble polymer structurants, plasticizers, rheology modifiers, other optional ingredients, and not more than about 60 wt % water; wherein the processing mixture has: a viscosity at 70° C. of from about 5,000 centipoise to about 150,000 centipoise;
  (b) fibrillating the processing mixture into fibers by a fluid film fibrillation process comprising a first pressurized gas stream directed against a liquid film of the processing mixture to form the fibers;
  (c) at least partially drying the fibers of the processing mixture by a second pressurized gas stream;
  (d) depositing the partially dry fibers on a surface to form a web of partially dry fibrous web structures; and
  (e) drying the partially dry fibrous web structure to a desired final moisture content.

The hydrophobic coating is then typically applied to the fibrous structure after the fibrous structure has been dried.

Suitable processes for making porous dissolvable solid structures in the form of a fibrous structure are described in detail in US 2012/0021026 A1, U.S. Application Ser. No. 61/982,469, and U.S. Application Ser No. 61/982,736.

Thickness and Shape of Porous Dissolvable Solid Structure

The porous dissolvable solid structure may take any shape including three-dimensional shapes with a plurality of outer-facing surfaces. Any of said outer-facing surfaces may be flat or curved or otherwise contoured. Said outer-facing surfaces may be opposing surfaces thereby comprising a top surface and a bottom surface, a front surface and a back surface, and/or a left surface and a right surface of said porous dissolvable solid structure. As used herein, the average distance between opposing outer-facing surfaces having highest surface area will be termed the "average thickness" of the porous dissolvable solid substrate.

Each outer-facing surface of the porous dissolvable solid structure may be in the form of a two-dimensional shape. Said two-dimensional shape may be any geometric shape including square, triangular, oval, circular, star-shapes or any other irregular shape including symmetric shapes and asymmetric shapes. In a preferred aspect, opposing outer-facing surfaces are of similar shape. In a preferred aspect, opposing outer-facing surfaces are ovals.

In one aspect, the average thickness of the porous dissolvable solid structure will be less than about 0.5 mm. In another aspect, the average thickness of the porous dissolvable solid structure is from about 0.5 mm to about 10 mm In another aspect, the average thickness of the porous dissolvable solid structure is greater than about 10 mm.

The porous dissolvable solid structure may be cut into individual portions or may be in the form of a continuous strip including delivered on a tape-like or toilet paper-like roll dispenser with individual portions dispensed via perforations and or a cutting mechanism.

The dissolvable porous solids of the present invention may take the form of one or more cylindrical objects, spherical objects, tubular objects or any other shaped object. In the case of cylindrical, spherical, or other objects with more of a third dimension versus a pad or strip, the thickness is taken as the maximum distance of the shortest dimension, e.g., the diameter of a sphere or cylinder.

Hydrophobic Coating

The consumer product of the present invention comprises a hydrophobic coating. The hydrophobic coating comprises one or more benefit agents. The benefit agent can comprise a variety of materials, such as conditioning agents, perfume, and the like.

The hydrophobic coating is applied to the porous dissolvable solid structure to form a consumer product of the present invention.

Depending upon the desired viscosity of the hydrophobic coating, the hydrophobic coating can further comprise viscosity modifiers, surfactants, or mixtures thereof. The hydrophobic coating is generally liquid in form at 25° C.

In one aspect, the hydrophobic coating consists of one benefit agent (e.g. only one benefit agent (such as a silicone) and no other components). In another aspect, the hydrophobic coating consists of two benefit agents (e.g. a first benefit agent and a second benefit agent, and no other components). In another aspect, as described in more detail below with regard to multiple benefit agents, the consumer product comprises two or more benefit agents, included in the same or in separate hydrophobic coating(s).

Benefit Agent

Any suitable hydrophobic benefit agent can be used. For instance, suitable benefit agents include conditioning agents, for example, hair conditioners, skin conditioners, or fabric conditioners, such as silicone, petrolatum, hydrocarbon oils (e g mineral oil), natural and synthetic waxes (e.g. microcrystalline waxes), paraffins, ozokerite, polyethylene, polybutene, polydecene, pentahydrosqualene, vegetable oils, triglycerides, fats, and combinations thereof. Furthermore, the benefit agent can be or can comprise perfume oil. Several benefit agents suitable for use herein are described below. The benefit agent is generally liquid in form at 25'C.

Conditioning Agents

Conditioning agents include any material which is used to give a particular conditioning benefit to hair and/or skin. In hair treatment compositions, suitable conditioning agents include those which deliver one or more benefits relating to shine, softness, comb-ability, antistatic properties, wet-handling, damage, manageability, body, and greasiness. The conditioning agents useful in the compositions of the present invention typically comprise a water insoluble, and non-volatile liquid. Suitable conditioning agents for use in the composition are those conditioning agents characterized generally as silicones (e.g., silicone oils, cationic silicones, silicone gums, high refractive silicones, functionalized silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Suitable conditioning agents are selected from the group consisting of silicones, organic conditioning oils, hydrocarbon oils, fatty esters, metathesized unsaturated polyol esters, silane-modified oils, other conditioning agents, and mixtures thereof.

The concentration of the conditioning agent in the composition should be sufficient to provide the desired conditioning benefits, and as will be apparent to one of ordinary skill in the art. Such concentration can vary with the conditioning agent, the conditioning performance desired, the type and concentration of other components, and other like factors.

Silicones

The conditioning agent of the compositions of the present invention is preferably a water-insoluble silicone conditioning agent. The silicone conditioning agent may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone material ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

Suitable silicones are selected from the group consisting of siloxanes, silicone gums, aminosilicones, terminal aminosilicones, alkyl siloxane polymers, cationic organopolysiloxanes, and mixtures thereof.

The concentration of the silicone conditioning agent typically ranges from about 0.5% to about 30%, in one aspect from about 1% to about 24%, in another aspect from about 2% to about 16%, and in another aspect from about 3% to about 8%. Non-limiting examples of suitable silicone conditioning agents, and optional suspending agents for the silicone, are described in U.S. Reissue Pat. No. 34,584, U.S. Pat. Nos. 5,104,646, and 5,106,609. The silicone conditioning agents for use in the compositions of the present invention can have a viscosity, as measured at 25° C., of from about 20 to about 2,000,000 centipoise ("cPs"), in one aspect from about 1,000 to about 1,800,000 cPs, in other aspects from about 50,000 to about 1,500,000 cPs, and in particular aspects from about 100,000 to about 1,500,000 cPs.

Background material on silicones including sections discussing silicone fluids, gums, and resins, as well as manufacture of silicones, is found in *Encyclopedia of Polymer Science and Engineering*, vol. 15, 2d ed., pp. 204-308, John Wiley & Sons, Inc. (1989).

The hair conditioning actives of the present invention may comprise one or more silicones including high molecular weight polyalkyl or polyaryl siloxanes and silicone gums; lower molecular weight polydimethyl siloxane fluids; and aminosilicones.

The high molecular weight polyalkyl or polyaryl siloxanes and silicone gums have a viscosity of from about 100,000 mPa·s to about 30,000,000 mPa·s at 25° C., in another aspect from about 200,000 mPa·s to about 30,000,000 mPa·s, and a molecular weight of from about 100,000 to about 1,000,000, and in some aspects from about 120,000 to about 1,000,000.

Preferred higher molecular weight silicone compounds useful herein include polyalkyl or polyaryl siloxanes with the following structure:

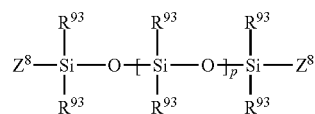

wherein $R^{93}$ is alkyl or aryl, and p is an integer from about 1,300 to about 15,000, more preferably from about 1,600 to about 15,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. Commercially available silicone compounds useful herein include, for example, those available from the General Electric Company in their TSF451 series, and those available from Dow Corning in their Dow Corning SH200 series.

The silicone compounds that can be used herein can also include a silicone gum. The term "silicone gum", as used herein, means a polyorganosiloxane material having a viscosity at 25° C. of greater than or equal to 1,000,000 mPa·s. It is recognized that the silicone gums described herein can also have some overlap with the above-disclosed silicone compounds. This overlap is not intended as a limitation on any of these materials. The "silicone gums" will typically have a mass molecular weight in excess of about 165,000, generally between about 165,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. Commercially available silicone gums useful herein include, for example, TSE200A and CF330M available from the General Electric Company.

The lower molecular weight silicones have a viscosity of from about 1 mPa·s to about 10,000 mPa·s at 25° C., in some aspects from about 5 mPa·s to about 5,000 mPa·s, and a molecular weight of from about 400 to about 65,000, and in some aspects from about 800 to about 50,000.

Preferred lower molecular weight silicone compounds useful herein include polyalkyl or polyaryl siloxanes with the following structure:

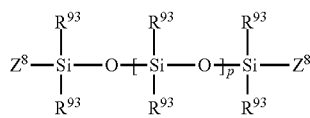

wherein $R^{93}$ is alkyl or aryl, and p is an integer from about 7 to about 850, more preferably from about 7 to about 665. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. Commercially available these silicone compounds useful herein include, for example, those available from the General Electric Company in their TSF451 series, and those available from Dow Corning in their Dow Corning SH200 series.

In one aspect, the active agent of the present invention includes one or more aminosilicones. Aminosilicones, as provided herein, are silicones containing at least one primary amine, secondary amine, tertiary amine, or a quaternary ammonium group. Preferred aminosilicones may have less than about 0.5% nitrogen by weight of the aminosilicone, more preferably less than about 0.2%, more preferably still, less than about 0.1%. Higher levels of nitrogen (amine functional groups) in the amino silicone tend to result in less friction reduction, and consequently less conditioning benefit from the aminosilicone. It should be understood that in some product forms, higher levels of nitrogen are acceptable in accordance with the present invention.

In a particular aspect, the aminosilicone has a viscosity of from about 1,000 centipoise ("cPs") to about 100,000 cPs, in another aspect from about 2,000 cPs to about 50,000 cPs, in yet another aspect from about 4,000 cPs to about 40,000 cPs, and in still another aspect from about 6,000 cPs to about 30,000 cPs. The viscosity of aminosilicones discussed herein is measured at 25° C.

The aminosilicone can be contained in the composition of the present invention at a level by weight of from about 0.5% to about 30%, in an alternate aspect from about 1.0% to about 24%, in another aspect from about 2.0% to about 16%, and in yet another aspect from about 3.0% to about 8%.

Examples of preferred aminosilicones for use in aspects of the subject invention include, but are not limited to, those which conform to the general formula (I):

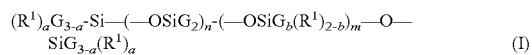

wherein G is hydrogen, phenyl, hydroxy, or $C_1$-$C_8$ alkyl, preferably methyl; a is 0 or an integer having a value from 1 to 3, preferably 1; b is 0, 1, or 2, preferably 1; wherein when a is 0, b is not 2; n is a number from 0 to 1,999; m is an integer from 0 to 1,999; the sum of n and m is a number from 1 to 2,000; a and m are not both 0; $R^1$ is a monovalent radical conforming to the general formula $C_qH_{2q}L$, wherein q is an integer having a value from 2 to 8 and L is selected from the following groups: —N($R^2$)$CH_2$—$CH_2$—N($R^2$)$_2$; —N($R^2$)$_2$; —N($R^2$)$^+_3$$A^-$; —N($R^2$)$CH_2$—$CH_2$—N $R^2H_2A^-$; wherein $R^2$ is hydrogen, phenyl, benzyl, or a saturated hydrocarbon radical, preferably an alkyl radical from about $C_1$ to about $C_{20}$; $A^-$ is a halide ion.

Some silicones for use herein can include those aminosilicones that correspond to formula (I) wherein m=0, a=1, q=3, G=methyl, n is preferably from about 1500 to about 1700, more preferably about 1600; and L is —N(CH$_3$)$_2$ or —NH$_2$, more preferably —NH$_2$. Other aminosilicones can include those corresponding to formula (I) wherein m=0, a=1, q=3, G=methyl, n is preferably from about 400 to about 600, more preferably about 500; and L is —N(CH$_3$)$_2$ or —NH$_2$, more preferably —NH$_2$. These aminosilicones can be called as terminal aminosilicones, as one or both ends of the silicone chain are terminated by nitrogen containing group.

An exemplary aminosilicone corresponding to formula (I) is the polymer known as "trimethylsilylamodimethicone", which is shown below in formula (II):

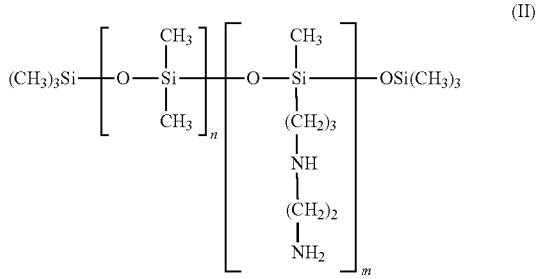

(II)

wherein n is a number from 1 to 1,999 and m is a number from 1 to 1,999.

The silicone may also be a terminal aminosilicone. "Terminal aminosilicone" as defined herein means a silicone polymer comprising one or more amino groups at one or both ends of the silicone backbone. In one aspect, the hydrophobic coating is substantially free of any silicone compound other than terminal aminosilicones.

In one aspect, the amino group at least one terminus of the silicone backbone of the terminal aminosilicone is selected from the group consisting of: primary amines, secondary amines and tertiary amines. The terminal aminosilicone may conform to Formula III:

III wherein G is hydrogen, phenyl, hydroxy, or $C_1$-$C_8$ alkyl, preferably methyl; a is an integer having a value from 1 to 3, or is 1; b is 0, 1 or 2, or is 1; n is a number from 0 to 1,999; $R_1$ is a monovalent radical conforming to the general formula $CqH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3$A$^-$; —N($R_2$)$CH_2$—$CH_2$—NR$_2$H$_2$A$^-$; wherein $R_2$ is hydrogen, phenyl, benzyl, or a saturated hydrocarbon radical; A$^-$ is a halide ion. In an aspect, $R_2$ is an alkyl radical having from 1 to 20 carbon atoms, or from 2 to 18 carbon atoms, or from 4 to 12 carbon atoms.

A suitable terminal aminosilicone corresponding to Formula III has a=1, q=3, G=methyl, n is from about 1000 to about 2500, alternatively from about 1500 to about 1700; and L is —N(CH$_3$)$_2$. A suitable terminal aminosilicone corresponding to Formula III has a=0, G=methyl, n is from about 100 to about 1500, or from about 200 to about, L is selected from the following groups: —N($R_2$)$CH_2$—$CH_2$—N($R_2$)$_2$; —N($R_2$)$_2$; —N($R_2$)$_3$A$^-$; —N($R_2$)$CH_2$—$CH_2$—NR$_2$H$_2$A$^-$; wherein $R_2$ is hydrogen, phenyl, benzyl, or a saturated hydrocarbon radical; A$^-$ is a halide ion, alternatively L is —NH$_2$. In an aspect, $R_2$ is an alkyl radical having from 1 to 20 carbon atoms, or from 2 to 18 carbon atoms, or from 4 to 12 carbon atoms. In an aspect, the terminal aminosilicone is selected from the group consisting of bis-aminomethyl dimethicone, bis-aminoethyl dimethicone, bis-aminopropyl dimethicone, bis-aminobutyl dimethicone, and mixtures thereof.

Suitable terminal aminosilicones include aminopropyl terminated polydimethylsiloxane (e.g. having a viscosity of 4,000-6,000 cSt (4-6 Pa·s); available under the tradename DMS-A35 from Gelest, Inc.), polydimethylsiloxane, trimethylsiloxy terminated (e.g. having a viscosity of 5,000 cSt (5 Pa·s); available under the tradename DMS-T35 from Gelest, Inc.), polydimethylsiloxane, trimethylsiloxy terminated (e.g. having a viscosity of 1,000 cSt (1 Pa·s); available under the tradename DMS-T31 from Gelest, Inc.), aminopropyl terminated polydimethylsiloxane (e.g. having a viscosity of 900-1,100 cSt (0.9-1.1 Pa·s); available under the tradename DMS-A31 from Gelest, Inc.), polydimethylsiloxane, trimethylsiloxy terminated (e.g. having a viscosity of 50 cSt (0.05 Pa·s); available under the tradename DMS-T15 from Gelest, Inc.), aminopropyl terminated polydimethylsiloxane (e.g. having a viscosity of 50-60 cSt (0.05-0.06 Pa·s); available under the tradename DMS-A15 from Gelest, Inc.), bis-aminopropyl dimethicone (e.g. having a viscosity of 10,220 cSt (10.2 Pa·s); available from Momentive Performance Materials Inc.), and mixtures thereof.

Alkyl Siloxane Polymer

Suitable conditioning agents as benefit agents of the hydrophobic coating further include alkyl siloxane polymers, as described in detail in US 2011/0243874 A1, US 2011/0243875 A1, US 2011/0240065 A1, US 2011/0243878A1, US 2011/0243871 A1, and US 2011/0243876 A1.

Cationic Organopolysiloxanes

Suitable conditioning agents as benefit agents of the hydrophobic coating further include cationic organopolysiloxanes, as described in detail in US 2014/0030206 A1, WO 2014/018985 A1, WO 2014/018986 A1, WO 2014/018987 A1, WO 2014/018988 A1, and WO 2014/018989 A1.

Organic Conditioning Oils

The conditioning component of the compositions of the present invention may also comprise from about 0.05% to about 3%, in one aspect from about 0.08% to about 1.5%, and in a particular aspect from about 0.1% to about 1%, of at least one organic conditioning oil as the conditioning agent, either alone or in combination with other conditioning agents, such as the silicones.

In one aspect, the hydrocarbon based benefit material comprises an average carbon chain length of greater than 20, in another aspect an average carbon chain length of greater than 30, and in still other aspects an average carbon chain length of greater than 40.

Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polyisobutylene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation. The concentration of such hydrocarbon oils in the composition can range from about 0.05% to about 20%, alternatively from about 0.08% to about 1.5%, and alternatively from about 0.1% to about 1%.

Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

Fatty Esters

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 22.

Still other fatty esters suitable for use in the compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acids, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters. Some preferred synthetic esters conform to the general Formula (IX):

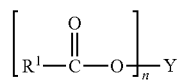

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (X):

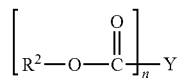

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (X).

Specific non-limiting examples of suitable synthetic fatty esters for use in the compositions of the present invention include: P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are available from Mobil Chemical Company.

Metathesized Unsaturated Polyol Esters

Other suitable organic conditioning oils as benefit agents include metathesized unsaturated polyol esters. Exemplary metathesized unsaturated polyol esters and their starting materials are set forth in US 2009/0220443 A1. A metathesized unsaturated polyol ester refers to the product obtained when one or more unsaturated polyol ester ingredient(s) are subjected to a metathesis reaction. Metathesis is a catalytic reaction that involves the interchange of alkylidene units among compounds containing one or more double bonds (i.e., olefinic compounds) via the formation and cleavage of the carbon-carbon double bonds. Metathesis may occur between two of the same molecules (often referred to as self-metathesis) and/or it may occur between two different molecules (often referred to as cross-metathesis).

Silane-Modified Oils

Other suitable organic conditioning oils as benefit agents include silane-modified oils. In general, suitable silane-modified oils comprise a hydrocarbon chain selected from the group consisting of saturated oil, unsaturated oil, and mixtures thereof; and a hydrolysable silyl group covalently bonded to the hydrocarbon chain. Suitable silane-modified oils are described in detail in U.S. Application Ser. No. 61/821,818, filed May 10, 2013.

Other Conditioning Agents

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal).

Perfume

The hydrophobic benefit agent of the present invention may also include one or more perfumes. The one or more perfumes may be selected from any perfume or perfume chemical suitable for topical application to the skin and/or hair and suitable for use in personal care compositions. The concentration of the perfume in the personal care composition should be effective to provide the desired aroma including, but not limited to, unscented. Generally, the concentration of the scented primary perfume is from about 0.5% to about 30%, in one aspect from about 1% to about 20%, in yet another aspect from about 2% to about 10%, and in yet another aspect from about 3% to about 8%, by weight of the solid article.

The perfume may be selected from the group consisting of perfumes, highly volatile perfume materials having a boiling point of less than about 250° C., and mixtures thereof. In one aspect, the perfume is selected from high impact accord perfume ingredients having a ClogP of greater than about 2 and odor detection thresholds of less than or equal to 50 parts per billion (ppb).

Viscosity Modifier

The hydrophobic coating of the present invention may comprise at least one viscosity modifier. A viscosity modifier is any material which may be incorporated into the hydrophobic coating that alters its rheological properties. Non-limiting examples of rheological properties that may be modified by the viscosity modifier include but are not limited to decreasing or increasing the viscosity of the hydrophobic coating and/or increasing or decreasing one or more yield-points of the hydrophobic coating and/or otherwise altering the shear characteristics of the hydrophobic coating. The viscosity modifier may be miscible in the hydrophobic coating.

Without being bound by theory it is believed that manipulating the rheological properties of the hydrophobic coating may impact the dispersibility of the hydrophobic coating during use. Specifically, decreasing the viscosity of the hydrophobic coating can lead to lower shear required to disperse the hydrophobic coating and/or yield smaller (yet still relatively large) particles of the dispersed hydrophobic coating in the aqueous liquor resulting from the dispersion of the consumer product of the present invention in an aqueous system. Alternately, increasing the viscosity of the hydrophobic coating may increase the particle size of the dispersed hydrophobic coating in the aqueous liquor resulting from the dispersion of the consumer product of the present invention in an aqueous system. As such, manipulating the viscosity of the hydrophobic coating is one means to manipulate the in-use requirements of the consumer product of the present invention and/or the particle size of the dispersed hydrophobic coating in the aqueous liquor resulting from the dispersion of the consumer product of the present invention in an aqueous system. Further, it is separately believed that increasing the particle size of the hydrophobic coating in said aqueous liquor may increase deposition of the benefit agent comprising said hydrophobic coating during use. As such, it is believed that manipulating the viscosity of the hydrophobic coating allows that the aqueous liquor resulting from the dispersion of the consumer product of the present invention in an aqueous system may be, on the one hand, more easily formed (e.g. decreased viscosity) or, on the other hand, more effectively deposited from said aqueous liquor during use (e.g. increased viscosity).

The viscosity modifier include, but are not limited to, the group consisting of vegetable oil, castor oil, petroleum distillates, hydrocarbon compounds, silicone compounds, esters of $C_6$-$C_{18}$ alkyl acetates, esters of $C_1$-$C_4$ carboxylic acid and $C_6$-$C_{18}$ alcohols, $C_6$-$C_{18}$ alkyl carbonates, $C_6$-$C_{18}$ diols, sterically hindered $C_6$-$C_{18}$ N-alkyl pyrrolidones and a-$C_1$-$C_4$ alkyl derivatives thereof, and mixtures thereof.

The viscosity modifier may a volatile or nonvolatile silicone compound, a volatile or nonvolatile hydrocarbon compound, or mixtures thereof. The volatile silicone compounds can be a linear or cyclic polydimethylsiloxane, such as hexamethylsiloxane or a cyclomethicone, available commercially under the trade names such as DOW CORNING 200 FLUID, DOW CORNING 244 FLUID, DOW CORNING 245 FLUID, DOW CORNING 344 FLUID, and DOW CORNING 345 FLUID from Dow Corning Corporation, Midland, Mich., and SILICONE SF-1173 and SILICONE SF-1202 from General Electric, Waterford, N.Y.

Volatile hydrocarbon compounds include hydrocarbons having about 10 to about 30 carbon atoms, for example, isododecane and isohexadecane, i.e., PERMETHYL 99A, PERMETHYL 101A, and PERMETHYL 102A, available from Presperse, Inc., South Plainfield, N.J. The volatile hydrocarbon compounds can also include aliphatic hydrocarbon having about 12 to about 24 carbon atoms, and having a boiling point of about 90° C. to about 250° C., i.e., ISOPAR C, ISOPAR E, ISOPAR G, and ISOPAR M, available from Exxon Chemical Co., Baytown, Tex. Other exemplary volatile hydrocarbon compounds are depicted in general structure (I):

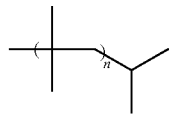

where n ranges from 2 to 5.

Additional viscosity modifiers include propylene carbonate, available commercially as ARCONATE PROPYLENE CARBONATE, available from ARCO Chemical Company, and hydrofluoroethers, available commercially as HFE-7100, HFE-71DE, HFE-71DA, HFE-71IPA, and HFE-7200, available from 3M Chemicals.

Nonvolatile hydrocarbon-based viscosity modifiers include mineral oil, a pheyltrimethicone, isopropyl myristate, castor oil, or branched hydrocarbons according to structure I where n is 5-250 including PERMETHYL 104A, PERMETHYL 106A, and PERMETHYL 108A, available from Presperse, Inc., South Plainfield, N.J. Nonvolatile viscosity modifiers also include polydimethylsiloxanes having a viscosity at 25° C. of about 6 to about 400 centipoise, such as DOW CORNING 556 FLUID, or DOW CORNING 200 FLUID, respectively, available from Dow Corning Corp., Midland, Mich.

Other viscosity modifiers that can be incorporated into the hydrophobic coating include, but are not limited to, branched 1-decene oligomers, like 1-decene dimer or polydecene; and esters having at least about 10 carbon atoms, and preferably about 10 to about 32 carbon atoms. Suitable esters include those comprising an aliphatic alcohol having about eight to about twenty carbon atoms, and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight-chained or branched. Preferably, the ester has a molecular weight of less than about 500. Suitable esters include, but are not limited to, a) aliphatic monohydric alcohol esters, including, but not limited to, myristyl propionate, isopropyl isostearate, isopropyl myristate, isopropyl palmitate, cetyl acetate, cetyl propionate, cetyl stearate, isodecyl neopentonoate, cetyl octanoate, isocetyl stearate; b) aliphatic di- and tri-esters of polycarboxylic acids, including, but not limited to, diisopropyl adipate, diisostearyl fumarate, dioctyl adipate, and triisostearyl citrate; c) aliphatic polyhydric alcohol esters, including, but not limited to, propylene glycol dipelargonate; d) aliphatic esters of aromatic acids, including, but not limited to $C_{12}$-$C_{15}$ alcohol esters of benzoic acid, octyl salicylate, sucrose benzoate, and dioctyl phthalate. Numerous other esters are listed in the International Cosmetic Ingredient Dictionary and Handbook, Vol. 2, Eight Ed., The Cosmetic Toiletry and Fragrance Assn., Inc., Washington, D.C. (2000) at pages 1670 through 1676, incorporated herein by reference.

The viscosity modifier may be a di- or tri-glyceride. Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

The viscosity modifier is generally at least partially miscible with at least one component of the hydrophobic coating.

The viscosity modifier comprises from about 1% to about 50%, more preferably from about 2% to about 40%, and most preferably from about 3% to about 30% by weight of the hydrophobic coating.

Hydrophobic Coating Surfactant

The hydrophobic coating of the present invention can optionally comprise surfactant. Incorporating surfactant in the hydrophobic coating may, upon dissolution of the consumer product, serve to reduce the interfacial tension between the hydrophobic portion and the aqueous portion of the aqueous treatment liquor resulting from dissolution of the consumer product. Further, by reducing this interfacial tension, the hydrophobic coating may be more easily dispersed in said aqueous liquor (e.g. requiring reduced shear).

In addition, in manipulating said interfacial tension, the resulting particle size of the dispersed benefit agent in the aqueous treatment liquor can be manipulated. To illustrate, reducing the interfacial tension may tend to reduce the particle size of the dispersed benefit agent in said aqueous treatment liquor and likewise decreasing the interfacial tension may tend to increase the particle size of the dispersed benefit agent in the aqueous treatment liquor. Further, increasing the particle size of benefit agent in said aqueous treatment liquor may tend to increase deposition of the benefit agent during use. As such, it is believed that manipulating the interfacial tension between the hydrophobic portion and the aqueous portion of the aqueous treatment liquor resulting from dissolution of the consumer product may allow, on the one hand, the dispersion to be more easily formed (e.g. decreased interfacial tension) or, on the other hand, the benefit agent to be more effectively deposited from said aqueous liquor during use (e.g. increased interfacial tension).

Suitable surfactants for inclusion within the hydrophobic coatings of the consumer products of the present invention include cationic, anionic, nonionic, amphoteric, zwitterionic surfactants and Gemini surfactants and combinations thereof.

Non-limiting examples of suitable cationic surfactants include quaternary ammonium salts, e.g., tetramethylammonium halides, alkyltrimethylammonium halides in which the alkyl group has from about 8 to 22 carbon atoms, for example octyltrimethylammonium chloride, dodecyltrimethylammonium chloride, hexadecyltrimethylammonium chloride, cetyltrimethylammonium chloride, and behenyltrimethylammonium chloride, benzyltrimethylammonium chloride, octyldimethylbenzyl-ammonium chloride, decetyldimethylbenzylammonium chloride, stearyldimethylbenzylammonium chloride, distearyldimethylammonium chloride, didodecyldimethylammonium chloride, dioctadecyldimethylammonium chloride, tallow trimethylammonium chloride, cocotrimethylammonium chloride, cetylpyridinium chloride and the other corresponding halides and hydroxides, and combinations thereof.

Non-limiting examples of non-ionic surfactants suitable for use in the compositions of the present invention include; condensation products of alcohols or phenols with alkylene oxides, mono- or di-alkyl alkanolamides, alkyl polyglycosides (APG's), esters of polyols and sugars, propylene oxide and ethylene oxide condensates, and combinations thereof.

Non-limiting examples of condensation products of alcohols or phenols with alkylene oxide include condensation products of aliphatic ($C_8$ to $C_{18}$) primary or secondary linear or branched chain alcohols or phenols with alkylene oxides, usually ethylene oxide, and generally having from 1 to 30 ethylene oxide groups, and combinations thereof.

Non-limiting examples of mono- or di-alkyl alkanolamides include mono- or di-alkyl alkanolamides include coco mono- or di-ethanolamide or coco-isopropanolamide, and combinations thereof.

Non-limiting examples of alkyl polyglycosides (APG's) include APG's that comprise an alkyl group connected (optionally via a bridging group) to a block of one or more glycosyl groups, and combinations thereof. Preferred APG's are described by the following formula:

$$RO\text{-}(G)_n$$

wherein R is a branched or straight chain alkyl group which may be saturated or unsaturated, and G is a saccharide group. R may represent a man alkyl chain length from about $C_5$ to about $C_{20}$. G may be selected from the group comprising glucose, xylose, fructose, mannose and derivatives thereof. Preferably, G is glucose. The degree of polymerization, n, may have a value of from about 1 to about 10 or more.

Non-limiting examples of esters of polyols and sugars include the polyethoxylated and/or polypropoxylated alkylphenols, the polyhydroxylated polyethers of fatty alcohols, fatty acid alkanolamides, amine oxides, and the condensation products of ethylene oxide with long chain amides, and combinations thereof.

Non-limiting examples of propylene oxide and ethylene oxide condensates include the Pluronic series produced by BASF.

Specific examples of the preferred nonionic surfactants include, but are not limited to, $C_8$-$C_{16}$ alkyl ethoxylates with two to seven ethoxylates, available commercially under trade names NEODOL 91-2.5E, NEODOL 91-5E, NEODOL 91-6E, NEODOL 91-8E, NEODOL 23-1.1E, NEODOL 23-2E, NEODOL 23-3E, NEODOL 23-6.5E, NEODOL 25-2.5E, NEODOL 25-3E, NEODOL 25-7E, NEODOL 25-9E, NEODOL 45-4E, and NEODOL 45-7E from Shell Chemical Company, Houston, Tex. Another specific example of a preferred nonionic surfactant includes, but is not limited to wherein the surfactant is a $C_{12}$ ethoxylate with 2-4 ethoxylates.

Non-limiting examples of amphoteric and zwitterionic surfactants suitable for use in compositions of the invention may include alkyl amine oxides, alkyl betaines, alkyl amidopropyl betaines, alkyl sulfobetaines, alkyl glycinates, alkyl carboxyglycinates, alkyl amphopropionates, alkulamphoglycinates, alkyl amidopropyl hydroxy-sultaines, acyl taurates and acyl glutamates, wherein the alkyl and acyl groups have from abut 8 to 19 carbon atoms. Examples include lauryl amine oxide, cocodimethyl sulphopropyl betaine and preferably lauryl betaine, cocamidopropyl betaine and sodium cocamphoproprionate.

Other amphoterics may be those of the dialkyl type including either phospholipids, i.e., based on glycerol and sphingosine, or glycolipid, i.e. based on sphingosine. Phospholipids are preferred with phosphatidyl choline (lecithin) being the preferred phospholipid. Of the alcohol moieties which comprise the phosphoglycerides, serine, choline and ethanolamine are particularly preferred, and of the fatty chains, those having a chain length of $C_{14}$ to $C_{24}$ are preferred. The fatty acid chains may be branched or unbranched, saturated or unsaturated, and palmitic, myristic, oleic, stearic, arachidonic, linolenic, linoleic and arachidic acids are particularly preferred.

Non-limiting examples of suitable anionic surfactants are the alkyl sulfonates, alkyl ether sulfonates, alkylaryl sulfonates, alkanoyl isethionates, alkyl succinates, alkyl sulfosuccinates, N-alkoyl sarcosinates, alkyl phosphates, alkyl ether phosphates, alkyl ether carboxylates, and alpha-olefin sulfonates, especially their sodium, magnesium, ammonium and mono-, di- and triethanolamine salts. The alkyl and acyl groups generally contain from 8 to 18 carbon atoms and may be unsaturated. The alkyl ether sulfates, alkyl ether phosphates and alkyl ether carboxylates may contain from one to 10 ethylene oxide or propylene oxide units per molecule. A preferred anionic surfactant includes, but is not limited to, alkyl and dialkyl sulfocuccinates such as sodium bis(2-ethylhexyl) sulfosuccinate, available commercially under trade name Aerosol OT from Mona Industries.

Gemini surfactants are made up of two hydrocarbon chains (generally, $C_{12}$-$C_{22}$) and two polar head groups linked by a short spacer. The spacer is attached directly to the polar head groups, each of which is in turn bonded to a hydrocarbon chain. The spacer can vary in length, hydrophobicity and flexibility and is typical a $C_2$-$C_5$ divalent alkyl radical. A typical Gemini surfactant is depicted as follows:

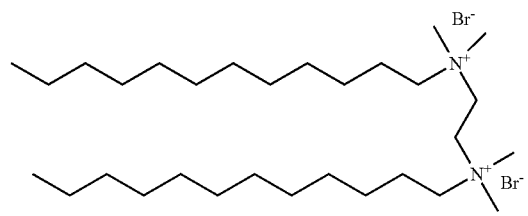 [SMILES: [Br-] ; CCCCCCCCCCCC[N+](C)(C)CC[N+](C)(C)CCCCCCCCCCCC ; [Br-]]

Gemini surfactants are also described further in the book: Surfactants and Polymers in Aqueous Solution, by Bo Jonsson, Bjorn Lindman, Krister Holmberg and Bengt Kronberg, pages 4-5, John Wiley and Sons, copyright 1998.

The hydrophobic coatings of the consumer products of the present invention may be comprised of one or more surfactants. The surfactant(s) may comprise from about 1 to 20% by weight, preferably from 2 to 10% by weight, more preferably from 3 to 5% by weight of the hydrophobic coating.

Viscosity of Hydrophobic Coating

The hydrophobic coating utilized in the present invention will generally have a viscosity of less than about 500 Pa·s (500,000 centipoise), less than about 350 Pa·s (350,000 centipoise), less than about 200 Pa·s (200,000 centipoise), less than about 100 Pa·s (100,000 centipoise), less than about 50 Pa·s (50,000 centipoise), or less than about 30 Pa·s (30,000 centipoise).

In one aspect, the hydrophobic coating will preferably have a viscosity of less than 14.5 Pa·s (14,500 centipoise), less than about 12 Pa·s (12,000 centipoise), less than about 11 Pa·s (11,000 centipoise), less than about 10 Pa·s (10,000 centipoise), less than about 5 Pa·s (5,000 centipoise), or less than about 1 Pa·s (1,000 centipoise).

If the viscosity of the hydrophobic coating is too high, upon dissolution of the dissolvable structure, the hydrophobic coating will tend not to sufficiently form the desired large particles and instead will tend to remain in a more continuous form. The relatively lower viscosity of the hydrophobic coating may facilitate more complete break-up of the hydrophobic coating during dissolution/use of the consumer product, particularly in use environments that include relatively lower shear. Further, it is believed that the relatively lower viscosity of the hydrophobic coating may also allow for faster break-up of the hydrophobic coating upon dissolution of the consumer product during use. It is further believed that both completeness and speed of break-up of the hydrophobic coating may be facilitated by introducing shear to the hydrophobic coating during use, particularly during the portion of use during which the porous dissolvable solid structure is being dissolved.

The viscosity of the hydrophobic coating is determined according to the VISCOSITY TEST METHOD described hereinbelow.

Thickness of Hydrophobic Coating

The hydrophobic coating of the present invention can be preferably applied to the porous dissolvable solid structure in a manner such that the average thickness and/or maximum thickness of the hydrophobic coating of the consumer product is less than about 1,000 micron, less than about 500 microns, less than about 100 microns, or less than about 50 microns. As used herein, the term "thickness" with respect to the hydrophobic coating means the distance between the solid structure outer-facing surface and the hydrophobic coating outer-facing surface.

As the porous dissolvable solid structure is porous, the hydrophobic coating may tend to migrate from the outer-facing surface of the porous dissolvable solid structure as applied into the interstitial pores of the porous dissolvable solid structure. In one aspect, the average thickness of the hydrophobic coating of the consumer product is zero, indicating that the hydrophobic coating may be fully migrated into the interstitial pores of the porous dissolvable solid structure.

The hydrophobic coating, if too thick, may fail to disperse adequately upon dissolution of the consumer product resulting in uneven distribution of the benefit agent(s) on the surface treated with the aqueous treatment liquor. This uneven distribution can result in consumer negatives such as spotting of fabrics or inadequate or uneven conditioning of hair. Minimizing the thickness of the hydrophobic coating can be particularly important when the viscosity of the hydrophobic coating is relatively high, e.g., at least about 10 Pa s, at least about 15 Pa s, at least about 100 Pa s, or at least about 300 Pa s.

The thickness of the hydrophobic coating is determined according to the THICKNESS OF HYDROPHOBIC COATING TEST METHOD hereinbelow.

Area Density of Application

The hydrophobic coating is preferably applied to the porous dissolvable solid structure in an amount and manner to provide an area density of application of the applied hydrophobic coating of less than about 250 micrograms (μg) per square millimeter ($mm^2$), preferably less than about 150 μg per $mm^2$, preferably less than about 120 μg per $mm^2$, preferably less than 100 μg per $mm^2$, of porous dissolvable solid structure. The area density of application of the hydrophobic coating is the weight of all materials in the hydrophobic coating(s), relative to the surface area of the porous dissolvable solid structure in the zone which is directly supporting that weight of hydrophobic coating. For purposes of determining the area density of application of the hydrophobic coating, the surface area of the porous dissolvable solid structure is considered to be planar and contiguous. As the porous dissolvable solid structure is porous, the hydrophobic coating may tend to migrate from the outer-facing surface of the porous dissolvable solid structure as applied into the interstitial pores of the porous dissolvable solid structure. If more than one surface of the porous dissolvable solid structure is coated, then the surface area of all the coated surfaces is used in the calculation. The hydrophobic coating has an area density of application that is reported in units of μg per $mm^2$.

If the amount of hydrophobic coating applied per area of dissolvable structure is too high, upon dissolution of the dissolvable structure, the hydrophobic coating will not sufficiently form the desired large particles and instead will tend to remain in a more continuous form. This can lead to the hydrophobic coating not effectively depositing on the treated surface or can lead to too much of the hydrophobic coating being deposited per area of treated surface, which in turn can lead to issues such as an undesireable hand feel (e.g. greasy feel) of the treated substrate or can lead to spotting of the treated surfaces (such as spotting of fabrics).

The hydrophobic coating may be applied to the porous dissolvable solid structure in any of a number of shapes including but not limited to geometric patterns such as stripes, dots, donut-shapes, triangles, rectangles, squares wavy-lines, arcs, z-patterns, and combinations thereof. Alternatively, the hydrophobic coating may be applied to the porous dissolvable solid structure so as to form representations of recognizable images such as flowers, birds, smiley-faces, and the like. Alternately, the hydrophobic coating may be applied to the porous dissolvable solid structure so as to form representations of commercial images such as logos, indicia, slogans and the like. Alternately, the hydrophobic coating may be applied to the porous dissolvable solid structure so as to form representations of letters and/or numbers including words that may comprise sayings, inspirational messages, jokes, or usage instructions.

Figure 1B:
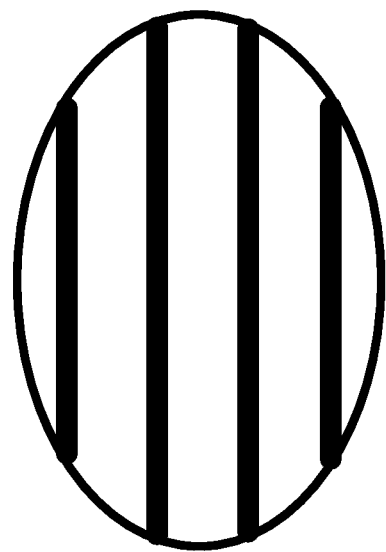

In a preferred aspect, the hydrophobic coating may be applied to the porous dissolvable solid structure as a plurality of stripes. FIGS. 1A and 1B represent a top-view of two non-limiting examples of an oval shaped consumer product comprising a porous dissolvable solid structure and a hydrophobic coating applied as stripes to the porous dissolvable solid structure (e.g. in 5-stripe and 4-stripe patterns).

The hydrophobic coating can be applied to the porous dissolvable solid structure via a variety of different processes known to those of skill in the art, such as slot coating, roll coating, nip coating, dip coating, knife coating, brush coating, printing (e.g. gravure printing, flexographic printing, inkjet printing, and the like), spraying, spiral/omega jet coating, and the like.

Loading

The consumer product of the present invention typically comprises hydrophobic coating applied to the porous dissolvable solid structure in an amount (i.e. total amount of hydrophobic coating(s)) of from about 1% to about 70%, from about 4% to about 70%, from about 5% to about 50%, from about 5% to about 30%, or from about 5% to about 20%, by weight of the consumer product.

Multiple Benefit Agents

In one aspect, the consumer product of the present invention can comprise two or more hydrophobic coatings, each comprising a benefit agent(s). In this aspect, each hydrophobic coating (e.g. a first hydrophobic coating, a second hydrophobic coating, etc.) is discretely applied to the porous dissolvable solid structure. The hydrophobic coatings can be applied on the same surface of the porous dissolvable solid structure or can be applied on different surfaces of the porous dissolvable solid structure. If applied on the same surface of the porous dissolvable solid structure, the hydrophobic coatings can be applied adjacent to one another. In this regard, the hydrophobic coatings can be directly adjacent (e.g. side-by-side), partially or completely overlap each other (e.g. a second hydrophobic coating discretely applied on top of a first hydrophobic coating), or be spaced apart (e.g. first and second hydrophobic coatings separated by surface area of the porous dissolvable solid structure without having any hydrophobic coating).

In one aspect, the consumer product of the present invention can comprise a hydrophobic coating that comprises two or more benefit agents. In this aspect, the benefit agents are preferably premixed together to form the hydrophobic coating, before the hydrophobic coating is applied to the porous dissolvable solid structure. In one aspect, the hydrophobic coating comprises silicone as a first benefit agent and perfume as a second benefit agent, wherein the silicone and perfume are premixed to form the hydrophobic coating, and then the hydrophobic coating is applied to the porous dissolvable solid structure.

In a preferred aspect, for example, the consumer product comprises a first hydrophobic coating comprising a silicone (e.g. a terminal aminosilicone) and a second hydrophobic coating comprising a perfume. In one aspect, the silicone coating is applied as spaced apart stripes and the perfume coating is applied as stripes adjacent and in-between the silicone coating stripes. In one aspect, the perfume coating is applied directed to the outer-facing surface of the porous dissolvable solid structure and the silicone coating is applied on top of the perfume coating (i.e. the silicone and perfume is not premixed). In one aspect, the silicone coating is applied on a top outer-facing surface and the perfume coating is applied on a bottom outer-facing surface of the porous dissolvable solid structure.

Method of Forming Aqueous Treatment Liquor

The present invention encompasses a method of forming an aqueous treatment liquor by dissolving the consumer product. The aqueous treatment liquor can be, for example, an aqueous laundry treatment liquor formed in a washing machine or hand-washing vessel, an aqueous hair treatment liquor formed by a consumer in the shower, an aqueous body treatment liquor formed by a consumer in the shower, an aqueous dish treatment liquor formed in a washing machine or hand-washing vessel, and the like.

The method generally comprises the steps of providing a consumer product of the present invention, providing an aqueous solution, and dissolving the consumer product in the aqueous solution. As the method steps are carried out, the dissolvable structure of the consumer product begins to dissolve in the aqueous solution. As the dissolvable structure dissolves away, the hydrophobic coating applied to the structure begins to break apart, thereby forming relatively large particles of benefit agent. It is the resulting relatively large particles of benefit agent in the aqueous treatment liquor that result in significant improvements in providing the desired benefits to the consumer of the consumer product, such as hair conditioning or fabric softening.

In forming the aqueous treatment liquor by dissolving the dissolvable structure of the consumer product, the method preferably further comprises the step of shearing of the aqueous treatment liquor. The shearing of the aqueous treatment liquor can be important to further facilitate breakup of the hydrophobic coating into the desired large particles. The shearing can be accomplished by mechanically manipulating (e.g. by machine or by hand) the aqueous treatment liquor (e.g. agitation), preferably during dissolution of the porous dissolvable solid structure. The shear rate can be tailored depending upon the method of treating the surface (e.g. machine vs. hand manipulation). In one aspect, the aqueous treatment liquor is sheared at a shear rate of from about 5 $s^{-1}$ to about 250 $s^{-1}$. In one aspect, the shear rate is zero $s^{-1}$.

In achieving the relatively large particles of benefit agent, factors such as viscosity of the hydrophobic coating, viscosity of the aqueous portion of the resulting aqueous treatment liquor, ratio of the viscosity of the hydrophobic coating to the viscosity of the aqueous portion of the aqueous treatment liquor, the viscosity of the hydrophobic portion in the resulting aqueous treatment liquor, and the like, can impact the effective formation of large benefit agent particles. The Capillary Number provided by the method, as described in detail below, can also impact the effective deposition of the large benefit agent particles on the treated surface, as the Capillary Number includes some of the above factors and others such as shear rate, droplet particle size, interfacial tension between the aqueous treatment liquor and the benefit agent, and the like.

The method of forming an aqueous treatment liquor comprising a benefit agent of the present invention comprises the steps of:
(a) providing a consumer product comprising:
 (i) a porous dissolvable solid structure, and
 (ii) a hydrophobic coating comprising a benefit agent, said hydrophobic coating applied to said porous dissolvable solid structure, wherein said hydrophobic coating has a first viscosity,
(b) providing an aqueous solution,
(c) dissolving said consumer product in said aqueous solution to form an aqueous treatment liquor comprising a hydrophobic portion and an aqueous portion, wherein said aqueous portion has a second viscosity,
wherein a ratio of said first viscosity to said second viscosity is less than about 100:1.

In one aspect, the method of forming an aqueous treatment liquor comprising a benefit agent comprises the steps of:
(a) providing a consumer product comprising:
 (i) a porous dissolvable solid structure, and
 (ii) a hydrophobic coating comprising a benefit agent, said hydrophobic coating applied to said porous dissolvable solid structure,
(b) providing an aqueous solution,
(c) dissolving said consumer product in said aqueous solution to form an aqueous treatment liquor,
wherein said method provides a Capillary Number of less than 1000.

In one aspect, the method of forming an aqueous treatment liquor comprising a benefit agent comprises the steps of:
(a) providing a consumer product comprising:
 (i) a porous dissolvable solid structure, and
 (ii) a hydrophobic coating comprising a benefit agent, said hydrophobic coating applied to said porous dissolvable solid structure,
(b) providing an aqueous solution,
(c) dissolving said consumer product in said aqueous solution to form an aqueous treatment liquor comprising a hydrophobic portion and an aqueous portion,
wherein said hydrophobic portion of said aqueous treatment liquor has a viscosity of less than about 14.5 Pa·s, preferably less than about 12 Pa·s, preferably less than about 11 Pa·s, preferably less than about 10 Pa·s, preferably less than about 5 Pa·s, and preferably less than about 1 Pa·s.

In one aspect, the method of forming an aqueous treatment liquor comprising a benefit agent comprises the steps of:
(a) providing a consumer product comprising:
 (i) a porous dissolvable solid structure, and
 (ii) a hydrophobic coating comprising a benefit agent, said hydrophobic coating applied to said porous dissolvable solid structure,
(b) providing an aqueous solution,
(c) dissolving said consumer product in said aqueous solution to form an aqueous treatment liquor,
wherein said aqueous treatment liquor comprises particles having a particle size of from about 10 microns to about 500 microns.

Particle Size in Aqueous Treatment Liquor

The methods of forming an aqueous treatment liquor of the present invention will preferably result in an aqueous treatment liquor comprising particles, e.g. benefit agent particles, having a particle size of from about 10 microns to about 500 microns, from about 30 microns to about 200 microns, from about 50 microns to about 150 microns, or from about 50 microns to about 100 microns. If the resulting particles in the aqueous treatment liquor have a particle size that is too small, then the benefit agent tends not to effectively deposit on the treated surface (especially without the use of other agents such as deposition aids and/or coacervates). For example, with respect to a laundry aqueous treatment liquor in a washing machine or a hair aqueous treatment liquor in the shower, the benefit agent will tend not to deposit on fabrics or hair and instead will tend to be rinsed down the drain. The consumer therefore will not realize the full potential benefits of the benefit agent.

If the resulting particles in the aqueous treatment liquor have a particle size that is too large, then the benefit agent tends to provide undesireable issues on the treated surface, such as undesireable hand feel (e.g. greasy feel) or spotting of the treated surface (such as spotting on fabrics).

The particle size of the particles, e.g. benefit agent particles, in the aqueous treatment liquor is determined according to PARTICLE SIZE TEST METHOD described hereinbelow. Note that the particle size ranges measured, reported, and claimed herein are based on radii (or equivalent radii) of the particles, rather than diameters (or equivalent diameters) of the particles.

Aqueous Portion of Aqueous Treatment Liquor Viscosity

The resulting aqueous treatment liquor of the present invention has an aqueous portion that preferably has a viscosity of from about 0.001 Pa·s to about 5 Pa·s.

It is believed that viscosity of the aqueous portion of the aqueous treatment liquor can impact the completeness and/or speed of break-up of the hydrophobic coating during use, particularly under shear conditions.

Increasing the viscosity of the aqueous portion of the aqueous treatment liquor tends to increase the efficiency of energy-transfer through the aqueous portion of the aqueous treatment liquor to the hydrophobic coating, thereby increasing completeness and/or speed of break-up of the hydrophobic coating during use, especially when the aqueous treatment liquor is sheared. The viscosity of the aqueous portion of the aqueous treatment liquor may be manipulated (e.g. increased), for example, by incorporating viscosity modifiers into the porous dissolvable solid structure, thereby increasing the viscosity of the aqueous portion of the aqueous treatment liquor upon dissolution of the consumer product.

In particular, it is believed that the relative viscosities of the hydrophobic coating and the aqueous portion of the aqueous treatment liquor may also impact the completeness and the speed of break-up of the hydrophobic coating during use, particularly under shear. For example, increasing the viscosity of the aqueous portion of the aqueous treatment liquor, relative to the viscosity of the hydrophobic coating, tends to increase completeness and/or speed of break-up of the hydrophobic coating during use, especially when the aqueous treatment liquor is sheared. As such, a relatively lower viscosity ratio of the viscosity of the hydrophobic coating to the viscosity of the aqueous portion of the aqueous treatment liquor can lead to more effective break-up of the hydrophobic coating.

The viscosity of the aqueous portion of the aqueous treatment liquor is determined according to the VISCOSITY TEST METHOD described hereinbelow.

Ratio of Hydrophobic Coating Viscosity to Aqueous Portion Viscosity

A ratio of the viscosity of the hydrophobic coating to the viscosity of the aqueous portion of the resulting aqueous treatment liquor is preferably less than about 100:1, less than about 50:1, less than about 10:1, less than about 5:1, or less than about 1:5.

As noted above, it is believed that dispersion of the hydrophobic coating as relatively large particles in the aqueous treatment liquor may be facilitated when the relative viscosities of the hydrophobic coating and the aqueous portion of the aqueous treatment liquor are such that the ratio of said viscosities is less than 100:1. It would be appreciated by one of ordinary skill in the art that this ratio can be impacted by either manipulating the viscosity of said hydrophobic coating and/or by manipulating said viscosity of the aqueous portion of said aqueous treatment liquor.

Capillary Number

In use, the consumer product of the present invention is dissolved in aqueous solution to form an aqueous treatment liquor. The hydrophobic coating of the consumer product tends to constitute a dispersed hydrophobic portion (e.g. as droplets) of the aqueous treatment liquor, while the porous dissolvable solid structure of the consumer product dissolves into the aqueous portion of the aqueous treatment liquor. In use, shearing forces apply a force to the aqueous treatment liquor. If the shear rate is large enough, then the force attempts to pull or stretch droplets of the hydrophobic portion. If stretched far enough, the droplets of hydrophobic portion will break into smaller droplets. At the same time, the droplets of hydrophobic portion try to resist stretching through the interfacial tension between the hydrophobic portion and the aqueous portion of the aqueous treatment liquor (as determined by the INTERFACIAL TENSION TEST METHOD described hereinbelow). These fluid flow dynamics are captured in the "Capillary Number". The Capillary Number is defined by the following equation:

$$Ca = \frac{r\mu \dot{v}}{\gamma}$$

wherein:
Ca is the Capillary Number (unitless),
r is the Radius of Sheared Hydrophobic Portion Droplets (in meters),
$\dot{v}$ is the fixed Shear Rate of 100 (in $s^{-1}$),
γ is the Interfacial Tension between the Aqueous Portion of the Aqueous Treatment Liquor and Hydrophobic Portion of the Aqueous Treatment Liquor (in $N \cdot m^{-1}$), and
μ is the Viscosity of the Aqueous Portion of the Aqueous Treatment Liquor (in Pa·s).

If the Capillary Number is relatively high, the force acting on the droplets of hydrophobic portion is relatively large and the droplets are likely to stretch and break into smaller droplets. If, on the other hand, the Capillary Number is relatively low, then the droplets tend to remain the same, relatively larger size in the aqueous treatment liquor.

It has been found that providing relatively larger particle size benefit agents in the aqueous treatment liquor herein can be achieved when the Capillary Number than is less than 1,000, preferably less than 500, preferably less than 300, or preferably less than 100. The relatively larger particle size benefit agents tend to deposit more effectively and therefore provide enhanced consumer benefits as compared to benefit agents having relatively small particle size.

The Capillary Number is determined according to the CAPILLARY NUMBER CALCULATION described hereinbelow.

Test Methods

The following test methods are conducted on samples that have been conditioned in a conditioned room at a temperature of 23° C.±2.0° C. and a relative humidity of 45%±10% for a minimum of 24 hours prior to testing. Except where noted, all tests are conducted under the same environmental conditions and in such conditioned room. Except where noted, all quantities are given on a weight basis. Except where noted all water used is laboratory-grade deionized (DI) water. Except where noted, at least three samples are measured for any given material being tested and the results from those three (or more) replicates are averaged to give the final reported value for that material, for that test.

Forming an Aqueous Treatment Liquor

For purposes of the test methods below, aqueous treatment liquor is generated according to the following procedure. The consumer product is combined with 38° C. deionized water in a glass container, at an article:water ratio of 1:7 (wt/wt). The container is sealed and loaded onto an orbital shaker mixing device, such as the VWR Model 3500, Catalog no. 89032-092 (VWR, Radnor, Pa., U.S.A.). The solution is then shaken for 24 hours at a speed setting of approximately 85 revolutions/min. The resulting solution is considered to be freshly-made, well-mixed aqueous treatment liquor, and any testing according to the test methods herein should be commenced immediately without storage of the aqueous treatment liquor.

The resulting aqueous treatment liquor will generally contain a hydrophobic portion(s) (e.g. typically containing the components of the hydrophobic coating(s), such as benefit agent(s)), and an aqueous portion (e.g. typically containing the components of the porous dissolvable solid structure). The hydrophobic portion(s) and aqueous portion of the aqueous treatment liquor can be isolated as follows. The aqueous treatment liquor is centrifuged at 4,500 g force for 30 minutes. Any layer(s) observed as separate from the main aqueous layer (i.e. the aqueous portion of the aqueous treatment liquor) after centrifugation is considered to be the hydrophobic portion(s) of the aqueous treatment liquor. Each layer is sampled individually and each sample is placed in a separate container.

Viscosity Test Method

The viscosity of a component of the consumer product (e.g. hydrophobic coating), or a component of an aqueous treatment liquor formed as indicated above (e.g. hydrophobic portion or aqueous portion of the aqueous treatment liquor), is determined as follows.

For a given component, the viscosity reported is the viscosity value as measured by the following method, which generally represents the zero-shear viscosity (or zero-rate viscosity) of the component. Viscosity measurements are made with an AR2000 Controlled-Stress Rheometer (TA Instruments, New Castle, Del., U.S.A.), and accompanying software version 5.7.0. The instrument is outfitted with a 40 mm stainless steel parallel plate (TA Instruments catalog no. 511400.901) and Peltier plate (TA Instruments catalog no. 533230.901). The calibration is done in accordance with manufacturer recommendations. A refrigerated, circulating water bath set to 25° C. is attached to the Peltier plate.

Measurements are made on the instrument with the following procedures: Conditioning Step (pre-condition the sample) under "Settings" label, initial temperature: 25° C., pre-shear at 5.0 $s^{-1}$ for 1 minute, equilibrate for 2 minutes; Flow-Step (measure viscosity) under "Test" Label, Test Type: "Steady State Flow", Ramp: "shear rate 1/s" from 0.001 $s^{-1}$ and 1000 $s^{-1}$, Mode: "Log", Points per Decade: 15, Temperate: 25° C., Percentage Tolerance: 5, Consecutive with Tolerance: 3, Maximum Point Time: 45 sec, Gap set to 1000 micrometers, Stress-Sweep Step is not checked; Post-Experiment Step under "Settings" label; Set temperature: 25° C.

More than 1.25 ml of the test sample of the component to be measured is dispensed through a pipette on to the center of the Peltier plate. The 40 mm plate is slowly lowered to 1100 micrometers, and the excess sample is trimmed away from the edge of the plate with a rubber policeman trimming tool or equivalent. Lower the plate to 1000 micrometers (gap setting) prior to collecting the data.

Discard any data points collected with an applied rotor torque of less than 1 micro-N·m (e.g. discard data less than ten-fold the minimum torque specification). Create a plot of viscosity versus shear rate on a log-log scale. These plotted data points are analyzed in one of three ways to determine the viscosity value:

first, if the plot indicates that the sample is Newtonian, in that all viscosity values fall on a plateau within +/−20% of the viscosity value measured closest to 1 micro-M·m, then the viscosity is determined by fitting the 'Newtonian' fit model in the software to all the remaining data;

second, if the plot reveals a plateau in which the viscosity does not change by +/−20% at low shear rates and a sharp, nearly-linear decrease in viscosity in excess of the +/−20% at higher shear rates, then the viscosity is determined by applying the "Best Fit Using Viscosity vs. Rate" option from the "Analysis Toolbar";

third, if the plot indicates that the sample is only shear-thinning, in that there is only a sharp, nearly-linear decrease in viscosity, then the material is characterized by a viscosity which is taken as the largest viscosity in the plotted data, generally a viscosity measured close to 1 micro-N·m of applied torque.

Report the average value of the replicates as the viscosity of the component, in units of Pa·s.

Thickness of Hydrophobic Coating Test Method

The thickness of a hydrophobic coating(s) on a porous dissolvable solid structure of the consumer product is determined using Field Emission Scanning Electron Microscopy (FE-SEM) equipped with Energy Dispersive X-ray Detection (EDS) for elemental analysis mapping. One such suitable instrument is the Hitachi S-4700 FE SEM (Field Emission Scanning Electron Microscope) (Hitachi High Technologies America Inc., Pleasanton, Calif., U.S.A.), equipped with Bruker SDD (Silicone Drift Detector) Esprit 1.9 for EDS mapping (Bruker Corp., Billerica, Mass., U.S.A.).

The consumer product is cut with a sharp razor blade and mounted such that the interior of the consumer product is observed in cross-sectional view (i.e., transverse view). Prior to imaging, the mounted sample of consumer product is covered with a thin conducting layer of gold and palladium via sputter deposition. The thickness of a hydrophobic coating of the consumer product is defined as the distance (in micrometers) between the outer-facing surface of the hydrophobic coating and the outer-facing surface of the porous dissolvable solid structure underneath the hydrophobic coating. Areas which appear to be uncoated are not to be measured, nor included in the average thickness value reported. The coating thickness is measured in at least 25 coated locations which are selected such that they are evenly distributed over the coated surface of the article. Report both the average thickness value and the maximum thickness value of the 25 thickness measurements made. If more than one surface of the porous dissolvable solid structure is coated, or if more than one type of coating is discernable, then an average and a maximum coating thickness is determined and reported separately for each surface or each coating type.

Particle Size Test Method

The particle size of particles (e.g. benefit agent particles) in an aqueous treatment liquor is determined as follows.

Generate a well-mixed aqueous treatment liquor in accordance with the method above. The particle size of the well-mixed aqueous treatment liquor is conducted using brightfield light microscopy.

One suitable light microscope is the Nikon Eclipse E600 POL microscope (Nikon Instruments Inc., Melville, N.Y., U.S.A.) equipped with a brightfield condenser, and with 10×, 20× and 40× objective lenses, plus a digital camera such as the Evolution VF Monochrome Model #01-Evolution VF-F-M-12, (Media Cybernetics, Rockville, Md., USA).

Two drops of the well-mixed aqueous treatment liquor are mounted under a coverslip on a standard glass microscope slide, and observed microscopically. An objective lens is selected which provides images wherein the size of the mean particle diameter is approximately 5-10% of the diameter of the field of view in the captured image. Representative images of the particles in the aqueous treatment liquor are captured by the digital camera until at least 100 representative particles have been photographed. Determine the radius of all representative particles in the captured images. For purposes of the particle size determination herein, the test method excludes air pockets/bubbles and solid particles such as encapsulated materials (e.g. perfume microcapsules), particle pigments, and the like.

One skilled in the art can apply image analysis software (such as Image-Pro Premier 64-bit, Ver.9.0.4 Build5139, 64-bit Media Cybernetics, Rockville, Md., USA, or equivalent) to detect and/or measure the dimensions of particles (objects) on the field (background). For particles which appear as approximately circular (spherical) objects in the images, measure their diameter then calculate and record the particle radius. For particles which appear distinctly non-circular (non-spherical) objects, determine the cross-sectional area of each particle in the image via image analysis software. For each area measurement, calculate the equivalent radius (which is the radius possessed by a circle having the same area as the particle's area). Calculate the mean of all measured radii and all calculated equivalent radii, to produce a single mean radius value across all the particles photographed in the sample, and report this radius in micrometers as the particle size of the hydrophobic portion of the aqueous treatment liquor.

Interfacial Tension Test Method

Interfacial tension (IFT) measurements are conducted between a hydrophobic portion of the aqueous treatment liquor and the aqueous portion of the aqueous treatment liquor using the pendant drop method. If it is impossible to create a drop in the pendant drop instrument (because the interfacial tension is too low), the measurements are then conducted by the spinning drop method.

The aqueous treatment liquor is generated according to the method hereinbefore. The aqueous portion and hydrophobic portion(s) of the aqueous treatment liquor are isolated according to the centrifugation method hereinbefore.

Using the pendant drop method, interfacial tension measurements are made by analyzing the shape of a pendant drop of a higher-density portion of the aqueous treatment liquor (e.g. typically a hydrophobic portion), suspended at the end of a capillary tube immersed in a lower-density portion of the aqueous treatment liquor (e.g. typically the aqueous portion). The pendant drop (hanging from a capillary tube) deforms under its own weight and an image of the drop is captured and analyzed. Comparison of the local curvature associated with the drop shape at different points along the curve provides a measure of the interfacial tension.

A suitable instrument for these IFT includes the Krüss Drop Shape Analysis System DSA100 (Krüss, Hamburg, Germany).

To conduct IFT measurements, it is necessary to first determine the density of the aqueous portion of the aqueous treatment liquor and the density of a hydrophobic portion of the aqueous treatment liquor. A suitable instrument for these density measurements is an Anton Paar DMA 4100 Density Meter (Anton Paar, Graz, Austria). Test sample of a given portion of the aqueous treatment liquor is loaded a 10-ml syringe and injected into the Density Meter. The injected sample is visually checked to ensure there are no air bubbles in the instrument prior to starting the measurement. The measured density of the sample is recorded from the instrument display panel.

To conduct pendant drop IFT measurements, the lower-density portion of the aqueous treatment liquor is brought to 22° C. inside the drop-shape analysis instrument reservoir. The higher-density portion of the aqueous treatment liquor is placed in instrument's capillary tube, and a small drop of the higher-density portion is extruded from the capillary tube into the reservoir. IFT measurements are obtained from images of the drop when its size is about 90% of its weight at detachment (as determined by the continuous addition of more fluid). An image is captured of the drop in silhouette. Three hundred points along the outline of the drop's silhouette are utilized by the instrument software as locations for data collection. At each point, the local pressure is determined from the local curvature. In comparing points at different heights, this pressure different is equated to the pressure difference associated with gravitational pressure (height differences). Comparison between two points provides one interfacial tension number; this is repeated over all three hundred points, resulting 150 measures of the interfacial tension. From this analysis the instrument reports a single mean value for the interfacial tension for a single drop. The process is repeated for a minimum of five drops. The average IFT value from the five or more replicates is reported, in units of $N \cdot m^{-1}$.

If a hydrophobic portion of the aqueous treatment liquor fails to form a pendant droplet at the end of the instruments capillary tube, and instead forms a stream of fluid, then the interfacial tension measurements are conducted via the spinning drop method. One instrument suitable for these spinning drop IFT measurements is the Krüss SITE04 Instrument (Krüss, Hamburg, Germany).

To conduct spinning drop IFT measurements (with hydrophobic portions which fail to form pendant droplets), a small drop of the lower-density portion of the aqueous treatment liquor is placed inside a barrel (or column) of the higher-density portion of the aqueous treatment liquor (or 'continuous phase'). The barrel is spun causing the drop to elongate along the axis of rotation. The resulting cross-sectional radius (normal to the axis of rotation) is linked to the interfacial tension as being proportional to the square of the rotation rate and the cube of the resulting radius.

To make these measurements, the higher-density portion (continuous phase) is brought to 22° C. in the barrel, and 3 µL of the lower-density portion is introduced into the barrel. The barrel is rotated at between 1,000-10,000 RPM. A minimum of five rotation speeds are selected that deform the drop such that $0.9 > R/R_o > 0.75$, where R is the short radius orthogonal to rotational axis at the rotational speed and $R_o$ is the radius of the drop at rest. At each rotational speed, the spinning is held for 10 minutes to equilibrate, the radius is measured and the interfacial tension is calculated. The reported interfacial tension value is the average of all values calculated at the different rotational speeds, and is expressed in units of N·m⁻¹.

Capillary Number Calculation

The Capillary Number is a dimensionless, calculated ratio which reflects the balance of viscous force to interfacial tension as related to the deformation and break up of drops in a sheared fluid. The Capillary Number (Ca) is expressed and calculated as:

$$Ca = \frac{r\mu\dot{v}}{\gamma}$$

wherein:
Ca is the Capillary Number (unitless),
r is the Radius of Sheared Hydrophobic Portion Droplets (in meters),
$\dot{v}$ is the fixed Shear Rate of 100 (in s⁻¹),
γ is the Interfacial Tension between the Aqueous Portion of the Aqueous Treatment Liquor and Hydrophobic Portion of the Aqueous Treatment Liquor (in N·m⁻¹), and
μ is the Viscosity of the Aqueous Portion of the Aqueous Treatment Liquor (in Pa·s).

The test methods for determining Viscosity (μ) and Interfacial Tension (γ) are described hereinabove. The test method for determining the Radius of the Sheared Hydrophobic Portion Droplets (r) is described herein below. The Shear Rate ($\dot{v}$) is a fixed constant as denoted above (100 s⁻¹, which originates from the operating conditions of the Linkam CSS450 optical shear stage rheometer, as used to measure the Radius of Sheared Hydrophobic Portion Droplets). The Capillary Number is then calculated from the equation above.

For purposes of calculating the Capillary Number, the Radius of Sheared Hydrophobic Portion Droplets ("r") is determined as follows.

Prepare a Linkam CSS450 optical shear stage rheometer (Linkam Scientific Instruments Ltd., Tadworth, Surrey, U.K.) by aligning the shear stage on a brightfield light microscope, such as an Nikon Eclipse LV100 POL Microscope (Nikon Instruments Inc., Melville, N.Y., U.S.A.) outfitted with a digital camera and a 10× objective lens, in accordance with all manufacturer manuals. Adjust the gap to 1.0 mm Load the sample materials into the optical rheometer in three layers, as follows. Add 0.75 ml of Aqueous Portion of the Aqueous Treatment Liquor to the base of a shear stage of the optical rheometer completely covering the base of the solution sample cell. Place one drop of a Hydrophobic Portion of the Aqueous Treatment Liquor on top of the Aqueous Portion, locating the Hydrophobic Portion droplet over the observation hole in the bottom of the solution cell (the observation hole is a distance of 7.5 mm outward from the rotational center of the stage). Add another 0.75 ml of Aqueous Portion of the Aqueous Treatment Liquor on top of these two layers. Replace the cover and tighten the screws. Shear the mixture at 100 s⁻¹ for 10 minutes.

Observe the resulting droplets through the microscope and capture representative images of the particles until at least 100 different particles have been photographed. Determine the radius of all representative particles in the captured images as follows.

One skilled in the art can apply image analysis software (such as Image-Pro Premier 64-bit, Ver.9.0.4 Build5139, 64-bit Media Cybernetics, Rockville, Md., USA, or equivalent) to detect and/or measure the dimensions of particles (objects) on the field (background). For particles which appear as approximately circular (spherical) objects in the images, measure their diameter then calculate and record the particle radius. For particles which appear distinctly non-circular (non-spherical) objects, determine the cross-sectional area of each particle in the image via image analysis software. For each area measurement, calculate the equivalent radius of the particle (which is the radius possessed by a circle having the same area as the particle's area).

Calculate the mean of all measured radii and calculated equivalent radii, to produce a single mean radius value across all the particles photographed in the sample. Report this radius in meters (m) as the Radius of Sheared Hydrophobic Portion Droplets, and use in the equation for calculating the Capillary Number above.

EXAMPLES

Examples 1-3

Porous Dissolvable Solid Structures

The following Examples 1-3 provide formulations for porous dissolvable solid structures in the form of open-cell foams according to the present invention.

Example 1

The following example relates to a porous dissolvable solid structure in the form of an open-cell foam.

| Raw Materials | % (wt/wt) | % of total as active | % actual | % of total minus water | % when dried |
|---|---|---|---|---|---|
| DI Water | 21.45% | 21.45% | 66.00% | | 0.00% |
| Glycerin (food grade) | 3.28% | 3.28% | 3.28% | 3.28% | 9.66% |
| Polyvinyl alcohol (Celvol 523) 85K-124K MW | 8.18% | 8.18% | 8.18% | 8.18% | 24.07% |
| Ammonium C11AS-N1 (28.0% Active) | 20.16% | 5.64% | 5.64% | 5.64% | 16.60% |
| Ammonium Laureth-1-Sulfate (ALE1S) (70% Active) | 8.06% | 5.64% | 5.64% | 5.64% | 16.60% |
| Ammonium Laureth-3-Sulfate (AE3S) (25% Active) | 4.98% | 1.25% | 1.25% | 1.25% | 3.66% |
| Mackam HPL-28ULS (Na LAA) (26% Active) | 32.27% | 8.39% | 8.39% | 8.39% | 24.68% |
| Citric Acid (anhydrous) | 1.61% | 1.61% | 1.61% | 1.61% | 4.73% |
| Total: | 100.00% | 55.45% | 100.00% | 34.00% | 100.00% |

A 2 kilogram capacity Bottom Line Process Technologies Cooker (available from Bottom Line Process Technologies, Largo, Fla.) with stir blade is used to prepare Example 1 premix. Distilled water and glycerin are weighed into the cooking container, which is then placed on the cooking apparatus. The blade is attached and set to stir the mixture at a speed setting of 30 (ca 48 rpm). The heating element is turned on and set for a target temperature of 75° C., and the polyvinyl alcohol (Celvol 523) is added slowly to the stirred water/glycerin mixture. Once the water/glycerin/Celvol 523 mixture reaches 75° C., mixing is continued an additional 10 minutes. Temperature is then set to 85° C., and the surfactants (Ammonium C11-AS, ALE1S, AE3S, and NaLAA) are added in order while stirring continued. After the addition of the surfactants, citric acid is added to reduce the pH to a range of 5.2 to 6.6. Once the mixture reaches 85° C., mixing is continued an additional 15 minutes, then the cooking container is removed from the cooking apparatus and set up to be stirred using an IKA RW20 ZM overhead mixer at a rate of 35 to 45 rpm until the mixture cooled to 45° C. Stirring is then stopped and the mixture is allowed to cool to room temperature. At room temperature, water lost via evaporation during the making process is added to the mixture and stirred until homogeneous. The pH is measured to ensure it is between 5.2 and 6.6.

A KitchenAid Mixer Model K5SS with flat beater and water bath attachments (available from Hobart Corporation, Troy, Ohio) is used to prepare the open-cell foam porous dissolvable solid structure. 300 grams of the premix is heated in an enclosed container in a 70° C. oven for 2-3 hours. About one liter of tap water is heated to 70° C. to 75° C., and the 5 quart stainless steel mixing bowl is preheated in the 70° C. oven. The premix is transferred to the preheated mixing bowl, which is then attached to the mixer stand. The flat beater and water bath are attached to the mixer stand, and the water bath is filled with the heated water. The premix is vigorously aerated at the highest setting of 10 for about 60 seconds to a target wet foam density of between 0.25 to 0.27 g/mL. The resulting wet foam is then transferred aluminum molds (16 cm×16 cm×6.5 cm) using a rubber spatula. A 12" metal spatula is used to spread and level the wet foam in the mold to 6.5 mm. The filled molds are placed in a 130° C. oven (Thermoscientific Precision Oven Model OVOOF) with high air flow to dry for about 40 minutes. The molds are then removed from the oven and placed in a 70° F./50% RH room to cool and equilibrate. The resulting foam is then removed from molds and cut to desired size and shape to form the open-cell foam porous dissolvable solid structure.

Example 2

The following example relates to a porous dissolvable solid structure in the form of an open-cell foam.

| Raw Materials | % (wt/wt) | % of total as active | % actual | % of total minus water | % when dried |
|---|---|---|---|---|---|
| DI Water | 35.03% | 35.03% | 69.42% | | 0.00% |
| Glycerin (food grade) | 2.97% | 2.97% | 2.97% | 2.97% | 9.70% |
| Polyvinyl alcohol (Celvol 523) 85K-124K MW | 7.39% | 7.39% | 7.39% | 7.39% | 24.18% |
| Ammonium C11AS-N1 (28% active) | 34.89% | 9.77% | 9.77% | 9.77% | 31.95% |
| Ammonium Laureth-1-Sulfate (ALE1S) (70% active) | 12.10% | 8.47% | 8.47% | 8.47% | 27.71% |
| Ammonium Laureth-3-Sulfate (AE3S) (25% active) | 7.51% | 1.88% | 1.88% | 1.88% | 6.14% |
| Citric Acid (Anhydrous) | 0.10% | 0.10% | 0.10% | 0.10% | 0.33% |
| Total: | 100.00% | 65.61% | 100.00% | 30.58% | 100.00% |

A 2 kilogram capacity Bottom Line Process Technologies Cooker (available from Bottom Line Process Technologies, Largo, Fla.) with stir blade is used to prepare Example 2 premix. Distilled water and glycerin are weighed into the cooking container, which is then placed on the cooking apparatus. The blade is attached and set to stir the mixture at a speed setting of 30 (ca 48 rpm). The heating element is turned on and set for a target temperature of 75° C., and the polyvinyl alcohol (Celvol 523) is added slowly to the stirred water/glycerin mixture. Once the water/glycerin/Celvol 523 mixture reaches 75° C., mixing is continued an additional 10 minutes. Temperature is then set to 85° C., and the surfactants (Ammonium C11-AS, ALE1S, and AE3S) are added in order while stirring continued. After the addition of the surfactants, citric acid is added to reduce the pH to a range of 5.2 to 6.6. Once the mixture reaches 85° C., mixing is continued an additional 15 minutes, then the cooking container is removed from the cooking apparatus and set up to be stirred using an IKA RW20 ZM overhead mixer at a rate of 35 to 45 rpm until the mixture cooled to 45° C. Stirring is then stopped and the mixture is allowed to cool to room temperature. At room temperature, water lost via evaporation during the making process is added to the mixture and stirred until homogeneous. The pH is measured to ensure it is between 5.2 and 6.6.

A KitchenAid Mixer Model K5SS with flat beater (available from Hobart Corporation, Troy, Ohio) is used to prepare the open-cell foam porous dissolvable solid structure. 250 grams of the premix is transferred to the 5 quart mixing bowl, which is then attached to the mixer stand. The flat beater is attached to the mixer stand. The premix is aerated at a setting of 6 for about 60 seconds to a target wet foam density of between 0.22 to 0.24 g/mL. The resulting wet foam is then transferred aluminum molds (16 cm×16 cm×6.5 cm) using a rubber spatula. A 12" metal spatula is used to spread and level the wet foam in the mold to 6.5 mm The filled molds are placed in a 130° C. oven (Thermoscientific Precision Oven Model OVOOF) with high air flow to dry for about 35 minutes. The molds are then removed from the oven and placed in a 70° F./50% RH room to cool and equilibrate. The resulting foam is then removed from molds and cut to desired size and shape to form the open-cell foam porous dissolvable solid structure.

Example 3

The following example relates to a porous dissolvable solid structure in the form of an open-cell foam.

| Raw Materials | % (wt/wt) | % of total as active | % actual | % of total minus water | % when dried | % when 90% dry |
|---|---|---|---|---|---|---|
| DI Water | 28.0067% | 28.0067% | 66.16% | | 0.00% | 10.00% |
| Jaguar C500 | 0.4000% | 0.4000% | 0.40% | 0.40% | 1.18% | 1.06% |
| Citric Acid (Anhydrous) | 1.4000% | 1.4000% | 1.40% | 1.40% | 4.14% | 3.72% |
| Mirapol AT1-AM Triquat (10% active) | 0.7500% | 0.0750% | 0.08% | 0.08% | 0.22% | 0.20% |
| Glycerin (food grade) | 3.2400% | 3.2400% | 3.24% | 3.24% | 9.57% | 8.62% |
| Polyvinyl alcohol (Celvol 523) 85K-124K MW | 8.0800% | 8.0800% | 8.08% | 8.08% | 23.87% | 21.48% |
| Mackam HPL-28ULS Sodium Lauroamphoacetate (LAA 22% active) | 37.0500% | 8.1510% | 8.15% | 8.15% | 24.08% | 21.67% |
| Sodium laureth-3-sulfate (28% active) | 5.3600% | 1.5008% | 1.50% | 1.50% | 4.43% | 3.99% |
| Sodium laureth-1-sulfate (70% active) | 15.7100% | 10.9970% | 11.00% | 11.00% | 32.49% | 29.24% |
| Yellow Dye #5 | 0.0033% | 0.0033% | 0.00% | 0.00% | 0.01% | 0.01% |
| | 100.0000% | 61.8505% | 100.00% | 33.85% | 100.00% | 100.00% |

This open-cell foam is made according to the process described in detail in US 2014/0105946 A1 at pages 2-4.

Examples 4-10

Hydrophobic Coatings

The following are various silicone materials that are useful as hydrophobic coatings which can be applied to the porous dissolvable solid structures herein. utilized as a hydrophobic coating and applied to a porous dissolvable solid structure as indicated to form non-limiting examples of consumer products.

Examples 11-31

Consumer Products

Consumer product examples are prepared using the example hydrophobic coating and open cell foam porous dissolvable solid structure according to the table below. In preparing each consumer product Example 11-31, 0.06 grams of the specified example hydrophobic coating are applied to the specified example open cell foam, wherein the open cell foam has an oval shape, a thickness of about 5 mm, a weight of 1.5 grams, and an outer-facing surface having a surface area of about 14.5 cm$^2$. The area density of application of the hydrophobic coating is about 40 µg/mm$^2$. The hydrophobic coating is applied uniformly to the top outer-facing surface of the open-cell foam using a brush. The resulting consumer products are useful as hair shampoo products.

| | CHEMICAL NAME | VISCOSITY | TRADENAME |
|---|---|---|---|
| EXAMPLE 4 | AMINOPROPYL TERMINATED POLYDIMETHYLSILOXANE | 4,000-6,000 cSt (4-6 Pa · s) | DMS-A35 from Gelest, Inc. |
| EXAMPLE 5 | POLYDIMETHYLSILOXANE, TRIMETHYLSILOXY TERMINATED | 5,000 cSt (5 Pa · s) | DMS-T35 from Gelest, Inc. |
| EXAMPLE 6 | POLYDIMETHYLSILOXANE, TRIMETHYLSILOXY TERMINATED | 1,000 cSt (1 Pa · s) | DMS-T31 from Gelest, Inc. |
| EXAMPLE 7 | AMINOPROPYL TERMINATED POLYDIMETHYLSILOXANE | 900-1,100 cSt (0.9-1.1 Pa · s) | DMS-A31 from Gelest, Inc. |
| EXAMPLE 8 | POLYDIMETHYLSILOXANE, TRIMETHYLSILOXY TERMINATED | 50 cSt (0.05 Pa · s) | DMS-T15 from Gelest, Inc. |
| EXAMPLE 9 | AMINOPROPYL TERMINATED POLYDIMETHYLSILOXANE | 50-60 cSt (0.05-0.06 Pa · s) | DMS-A15 from Gelest, Inc. |
| EXAMPLE 10 | BIS-AMINOPROPYL DIMETHICONE | 10,220 cPs (10.2 Pa · s) | Available from Momentive Performance Materials Inc. |

| CONSUMER PRODUCT | HYDROPHOBIC COATING | OPEN CELL FOAM |
|---|---|---|
| EXAMPLE 11 | EXAMPLE 4 | EXAMPLE 2 |
| EXAMPLE 12 | EXAMPLE 5 | EXAMPLE 2 |
| EXAMPLE 13 | EXAMPLE 6 | EXAMPLE 2 |
| EXAMPLE 14 | EXAMPLE 7 | EXAMPLE 2 |
| EXAMPLE 15 | EXAMPLE 8 | EXAMPLE 2 |
| EXAMPLE 16 | EXAMPLE 9 | EXAMPLE 2 |
| EXAMPLE 17 | EXAMPLE 10 | EXAMPLE 2 |
| EXAMPLE 18 | EXAMPLE 4 | EXAMPLE 3 |
| EXAMPLE 19 | EXAMPLE 5 | EXAMPLE 3 |
| EXAMPLE 20 | EXAMPLE 6 | EXAMPLE 3 |
| EXAMPLE 21 | EXAMPLE 7 | EXAMPLE 3 |
| EXAMPLE 22 | EXAMPLE 8 | EXAMPLE 3 |
| EXAMPLE 23 | EXAMPLE 9 | EXAMPLE 3 |
| EXAMPLE 24 | EXAMPLE 10 | EXAMPLE 3 |
| EXAMPLE 25 | EXAMPLE 4 | EXAMPLE 1 |
| EXAMPLE 26 | EXAMPLE 5 | EXAMPLE 1 |
| EXAMPLE 27 | EXAMPLE 6 | EXAMPLE 1 |
| EXAMPLE 28 | EXAMPLE 7 | EXAMPLE 1 |
| EXAMPLE 29 | EXAMPLE 8 | EXAMPLE 1 |

-continued

| CONSUMER PRODUCT | HYDROPHOBIC COATING | OPEN CELL FOAM |
|---|---|---|
| EXAMPLE 30 | EXAMPLE 9 | EXAMPLE 1 |
| EXAMPLE 31 | EXAMPLE 10 | EXAMPLE 1 |

Examples 32-35

The following are further non-limiting examples of formulations of consumer products of the present invention. Examples 32-33 relate to open-cell foam consumer products whereas Examples 34-35 relate to fibrous web consumer products. The resulting consumer products have an oval shape and weight about 1.5 grams. The consumer products are useful as hair shampoo products.

Example 32

| Trade name | INCI name | % active in premix | calculated dry pad (%) assuming 10% water | basis mass (g) = 1.5 g | calculated dry pad (%) after hydrophobic coating addition |
|---|---|---|---|---|---|
| Distilled Water | Water | 66.00 | 10.00% | 0.15 | 8.32% |
| Glycerol | Glycerin-USP | 3.24 | 8.57% | 0.13 | 7.14% |
| Jaguar C500 | Guar hydroxypropyltrimonium Chloride | 0.40 | 1.06% | 0.02 | 0.88% |
| Mirapol AT-1 | Polyquatenium 76 | 0.08 | 0.20% | 0.00 | 0.17% |
| Celvol 523 | Polyvinyl Alcoho (85-124K mwt.) | 8.08 | 21.38% | 0.32 | 17.79% |
| Mackam HPL-28ULS (22% Active) | Sodium Lauroamphoacetate | 8.15 | 21.57% | 0.32 | 17.96% |
| Sodium Laureth 1 Sulfate | Sodium Laureth (1) Sulfate | 11.00 | 29.12% | 0.44 | 24.24% |
| Sodium Laureth 3 Sulfate | Sodium Laureth (3) Sulfate | 1.50 | 3.97% | 0.06 | 3.31% |
| Citric Acid | Citric Acid | 1.50 | 3.97% | 0.06 | 3.31% |
| FD&C Yellow #5 | yellow #5 (CI 19140) | 0.0033 | 0.01% | 0.00 | 0.01% |
| D/DL Panthenyl Ethyl Ether | Panthenol Ethyl Ether | 0.03 | 0.08% | 0.00 | 0.07% |
| DL Panthenol | Panthenol | 0.03 | 0.07% | 0.00 | 0.06% |
| Terminal Amino Silicone | Bis-aminopropyl Dimethicone[1] | | | 0.102 | 5.66% |
| Perfume | Perfume | | | 0.2 | 11.10% |
| Water is QS | | | | | |

[1] Available from Momentive Performance Materials Inc. having a viscosity of 10,220 cPs (10.2 Pa · s)

Example 33

| Trade name | INCI name | Activity | % as added in premix | mass added (g) | % active in premix | calculated dry pad (%) assuming 10% water | basis mass (g) = 1.5 g | calculated dry pad (%) after hydrophobic coating addition |
|---|---|---|---|---|---|---|---|---|
| Distilled Water | Water | 100% | 24.70 | | 63.34 | 10.00% | 0.15 | 8.94% |
| Glycerol | Glycerin-USP | 100% | 3.80 | | 3.80 | 9.33% | 0.14 | 8.34% |
| Jaguar C500 | Guar hydroxypropyltrimonium Chloride | 100% | 0.20 | | 0.20 | 0.49% | 0.01 | 0.44% |
| Modified Cationic Guar | Guar hydroxypropyltrimonium Chloride | 100% | 0.30 | | 0.30 | 0.74% | 0.01 | 0.66% |
| PVA 420H | Polyvinyl Alcohol (80H/75M)) | 100% | 5.74 | | 5.74 | 14.09% | 0.21 | 12.61% |
| PVA 403 | Polyvinyl Alcohol (80H/30M) | 100% | 2.46 | | 2.46 | 6.04% | 0.09 | 5.40% |

-continued

| Trade name | INCI name | Activity | % as added in premix | mass added (g) | % active in premix | calculated dry pad (%) assuming 10% water | basis mass (g) = 1.5 g | calculated dry pad (%) after hydrophobic coating addition |
|---|---|---|---|---|---|---|---|---|
| Mackam HPL-28ULS (22% Active) | Sodium Lauroamphoacetate | 22% | 38.18 | | 8.40 | 20.62% | 0.31 | 18.45% |
| Sodium Laureth 1 Sulfate | Sodium Laureth (1) Sulfate | 70% | 16.00 | | 11.20 | 27.50% | 0.41 | 24.60% |
| Sodium Laureth 3 Sulfate | Sodium Laureth 3 Sulfate | 28% | 5.36 | | 1.50 | 3.68% | 0.06 | 3.30% |
| Cocamide MEA | Coco monoethanolamine | 85% | 1.76 | | 1.50 | 3.67% | 0.06 | 3.29% |
| Citric Acid | Citric Acid | 100% | 1.50 | | 1.50 | 3.68% | 0.06 | 3.29% |
| FD&C Yellow #5 | yellow #5 (CI 19140) | 100% | 0.0040 | | 0.00 | 0.01% | 0.00 | 0.01% |
| D/DL Panthenyl Ethyl Ether | Panthenol Ethyl Ether | 100% | 0.0300 | | 0.03 | 0.07% | 0.00 | 0.07% |
| DL Panthenol | Panthenol | 50% | 0.0536 | | 0.03 | 0.07% | 0.00 | 0.06% |
| Terminal Amino Silicone | Bis-aminopropyl Dimethicone[1] | 100% | (added to dry pad) | 0.102 | | | 0.10 | 6.08% |
| Perfume | Perfume | 100% | (added to dry pad) | 0.075 | | | 0.08 | 4.47% |
| Water is QS | | | | | | | | |

[1]Available from Momentive Performance Materials Inc. having a viscosity of 10,220 cPs (10.2 Pa · s)

Example 34

| Trade name | INCI name | % as added in premix | mass added (g) | % active in premix | calculated dry pad (%) assuming 10% water | basis mass (g) = 1.3 g | calculated dry pad (%) after hydrophobic coating addition |
|---|---|---|---|---|---|---|---|
| Distilled Water | Water | 61.4221 | | | 9.09% | 0.11 | 7.11% |
| Citric Acid | Citric Acid | 0.39 | | | | | 1.84% |
| Sodium Benzoate | Sodium Benzoate | 0.17 | | 0.17 | 0.92% | 0.01 | 0.78% |
| Jaguar C500 | Guar hydroxypropyltrimonium Chloride | 0.51 | | 0.51 | 2.84% | 0.04 | 2.39% |
| Mirapol AT-1 | Polyquaternium 76 | 0.10 | | 0.01 | 0.05% | 0.00 | 0.04% |
| PVA420H | Polyvinyl Alcohol | 5.28 | | | | 0.00 | 0.00% |
| PVA403 | Polyvinyl Alcohol | 5.28 | | 5.28 | 29.19% | 0.38 | 24.53% |
| Mackam LHS (50% Active) | Lauryl Hydroxysultaine | 6.24 | | 1.62 | 8.97% | 0.12 | 7.54% |
| Sodium Laureth 1 Sulfate | Sodium Laureth (1) Sulfate | 12.00 | | 8.40 | 46.43% | 0.60 | 39.02% |
| Sodium Laureth 3 Sulfate | Sodium Laureth (3) Sulfate | 1.62 | | 0.45 | 2.51% | 0.03 | 2.11% |
| Na-C11 | Sodium Undecyl Sulfate | 7.38 | | | | 0.00 | 0.00% |
| Terminal Amino Silicone | Bis-aminopropyl Dimethicone[1] | 0.0000 | 0.105 | | 0.00% | 0.105 | 6.79% |
| Perfume | Perfume | 0.0000 | 0.150 | | 0.00% | 0.15 | 10.74% |
| Water is QS | | | | | | | |

[1]Available from Momentive Performance Materials Inc. having a viscosity of 10,220 cPs (10.2 Pa · s)

Example 35

| Trade name | INCI name | % as added in premix | % active in premix | calculated dry pad (%) assuming 10% water | basis mass (g) = 1.3 g | calculated dry pad (%) after minor addition |
|---|---|---|---|---|---|---|
| Distilled Water | Water | 1.800 | 49.5700 | 19.67% | 0.11 | 9.53% |
| PVA420H | Polyvinyl Alcohol (80% hydrolyzed) | 9.000 | 3.1625 | | | 1.84% |
| PVA403 | Polyvinyl Alcohol (80% hydrolyzed) | 36.200 | 12.6625 | 24.35% | 0.32 | 27.43% |
| LR400 | Cationic hydroxyethyl cellulose | 0.500 | 0.5000 | 0.96% | 0.01 | 1.08% |
| LAPB | Lauramidopropyl Betaine | 13.900 | 5.0000 | | 0.00 | 0.00% |
| Isalchem 123AS | Sodium Lauryl (branched) Sulfate | 37.900 | 28.4375 | 54.69% | 0.71 | 61.60% |
| Sodium Benzoate | Sodium Benzoate | 0.167 | 0.1670 | 0.32% | 0.00 | 0.36% |
| Citric Acid (Anhydrous) | Citric Acid (Anhydrous) | 0.500 | 0.5000 | | 0.00 | 0.00% |
| Terminal Amino Silicone | Bis-aminopropyl Dimethicone[1] | 0.0000 | | 0.00% | 0.105 | 7.45% |
| Fragrance Water is QS | Royal Hue | 0.0000 | | 0.00% | 0.15 | 10.64% |

[1]Available from Momentive Performance Materials Inc. having a viscosity of 10,220 cPs (10.2 Pa · s)

Comparative Example A

A comparative example of a consumer product comprising porous dissolvable solid structure in the form of a open-cell foam coated with dimethicone having a viscosity of 346,500 cPs (346 Pas) (available under the tradename CF330M from Momentive Performance Materials Inc.) is prepared according to Example 2 as described in US 2010/0291165 A1 at pages 17-18.

Comparative Example B

A comparative example of consumer product is prepared as in Comparative Example A except that dimethicone is substituted with aminosilicone having a viscosity of 14,500 cPs and an amine content of 0.050 meq/g (Product Code 65850 Y-14945 available from Momentive Performance Materials Inc.).

Comparative Example C

A comparative example of a consumer product comprising a porous dissolvable solid structure in the form of an open-cell foam coated with dimethicone having a viscosity of 346,500 cPs (346 Pas) (available under the tradename CF330M from Momentive Performance Materials Inc.) is prepared according to Example 4 as described in US 2010/0291165 A1 at pages 18-19.

Comparative Example D

A comparative example of consumer product is prepared as in Comparative Example C except that dimethicone is substituted with aminosilicone having a viscosity of 14,500 cPs and an amine content of 0.050 meq/g (Product Code 65850 Y-14945 available from Momentive Performance Materials Inc.).

Capillary Number vs. Viscosity Ratio

The consumer products of Examples 11-31 and the Comparative Examples A-D are each dissolved in aqueous solution to form aqueous treatment liquors according to the test method described hereinbefore. Each aqueous treatment liquor is tested according to the test methods and CAPILLARY NUMBER CALCULATION description above and the Capillary Number of each is reported. The viscosity of the hydrophobic portion and the viscosity of the aqueous portion of each aqueous treatment liquor is measured according to the VISCOSITY TEST METHOD described hereinbefore. A Viscosity Ratio of the hydrophobic portion viscosity to the aqueous portion viscosity is calculated for each aqueous treatment liquor. The following data is plotted in FIG. 2 as Capillary Number vs. Viscosity Ratio:

| | CAPILLARY NUMBER | VISCOSITY RATIO |
|---|---|---|
| EXAMPLE 11 | 93.5 | 25.5 |
| EXAMPLE 12 | 8.7 | 31.8 |
| EXAMPLE 13 | 55.8 | 6.4 |
| EXAMPLE 14 | 14 | 6.4 |
| EXAMPLE 15 | 235 | 0.3 |
| EXAMPLE 16 | 2 | 0.2 |
| EXAMPLE 17 | 6.6 | 146 |
| EXAMPLE 18 | 27.6 | 13.5 |
| EXAMPLE 19 | 2.2 | 16.6 |
| EXAMPLE 20 | 1.6 | 3.2 |
| EXAMPLE 21 | 14.9 | 3.2 |
| EXAMPLE 22 | 73 | 0.2 |
| EXAMPLE 23 | 119 | 0.1 |
| EXAMPLE 24 | 4.3 | 77.6 |
| EXAMPLE 25 | 5.8 | 25.5 |
| EXAMPLE 26 | 1.4 | 31.3 |
| EXAMPLE 27 | 0.6 | 6.1 |
| EXAMPLE 28 | 12.7 | 6 |
| EXAMPLE 29 | 44.8 | 0.3 |

| | CAPILLARY NUMBER | VISCOSITY RATIO |
|---|---|---|
| EXAMPLE 30 | 222.6 | 0.21 |
| EXAMPLE 31 | 6 | 146 |
| COMPARATIVE EXAMPLE A | 4725 | 3261 |
| COMPARATIVE EXAMPLE B | 3281 | 273 |
| COMPARATIVE EXAMPLE C | 6850 | 1520 |
| COMPARATIVE EXAMPLE D | 1312 | 127 |

Figure 2:
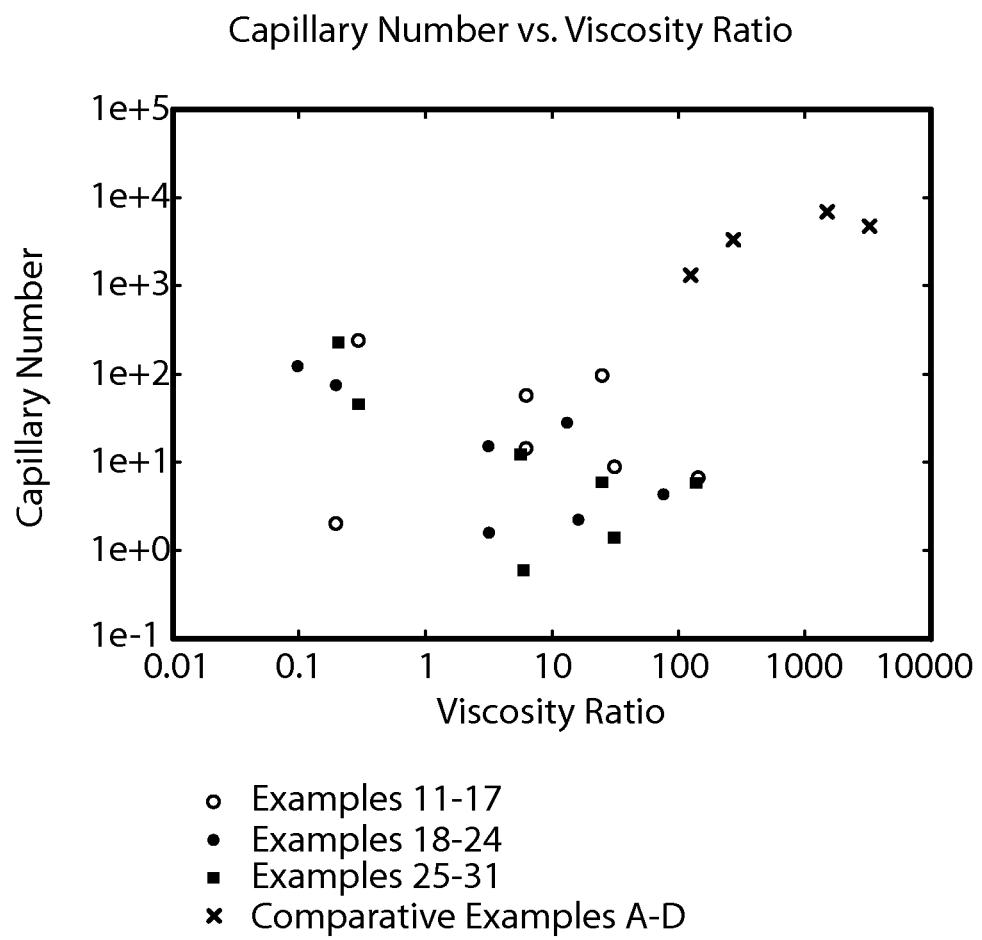
FIG. 2 is a plot of Viscosity Ratio versus Capillary Number exhibited by consumer products of the present invention, as well as comparative examples of consumer products.

As can be seen in FIG. 2, from the above data, the aqueous treatment liquors formed from Examples 11-31 exhbit preferred Capillary Numbers and Viscosity Ratios (and combinations thereof) relative to the aqueous treatment liquors formed from Comparative Examples A-D. These preferred Capillary Numbers and Viscosity Ratios result in relatively larger particle size particles (e.g. benefit agent particles) in the aqueous treatment liquor, which tend to deposit much more effectively on the treat surfaces, thereby enhancing the consumer benefits provided by the benefit agents.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of forming an aqueous treatment liquor comprising a benefit agent, said method comprising the steps of:
   (a) providing a consumer product comprising:
      (i) a porous dissolvable solid structure, wherein said porous dissolvable solid structure is in the form of fibrous web structure, and
      (ii) a hydrophobic coating comprising two or more benefit agents, wherein a first benefit agent and a second benefit agent are premixed to form said hydrophobic coating prior to said hydrophobic coating being applied to said porous dissolvable solid structure, wherein said hydrophobic coating has a first viscosity;
   (b) providing an aqueous solution;
   (c) dissolving said consumer product in said aqueous solution to form an aqueous treatment liquor comprising a hydrophobic portion and an aqueous portion, wherein said aqueous portion has a second viscosity; and
   (d) shearing said aqueous treatment liquor;
   wherein a ratio of said first viscosity to said second viscosity is less than about 100:1; and wherein said aqueous treatment liquor comprises particles having a partible size of from about 10 microns to about 500 microns.

2. The method of claim 1, wherein said ratio of said first viscosity to said second viscosity is less than about 50:1.

3. The method of claim 1, wherein said first viscosity is less than about 500 Pa·s.

4. The method of claim 1, wherein said first viscosity is less than about 14.5 Pa·s.

5. The method of claim 1, wherein said second viscosity is from about 0.001 Pa·s to about 5 Pa·s.

6. The method of claim 1, wherein said method provides a Capillary Number of less than about 1000.

7. The method of claim 1, wherein said hydrophobic coating of said consumer product has an average thickness and/or maximum thickness of less than about 1000 microns.

8. The method of claim 1, wherein said consumer product is selected from the group consisting of a beauty care product, hand washing product, body wash product, shampoo product, conditioner product, cosmetic product, hair removal product, laundry product, laundry rinse additive product, laundry detergent product, hard surface cleaning product, hand dishwashing product, automatic dishwashing product, and unit dose form automatic dishwashing or laundry product.

9. The method of claim 1, wherein said consumer product comprises said hydrophobic coating applied to said porous dissolvable solid structure in an amount of from about 1% to about 70%, by weight of the consumer product.

10. The method of claim 1, wherein said hydrophobic coating has an area density of application of less than about 250 µg per mm$^2$ of said porous dissolvable solid structure.

11. The method of claim 1, wherein said benefit agent of said hydrophobic coating is selected from the group consisting of conditioning agent, perfume, and mixtures thereof.

12. The method of claim 11, wherein said conditioning agent is selected from the group consisting of silicones, organic conditioning oils, hydrocarbon oils, fatty esters, metathesized unsaturated polyol esters, silane-modified oils, and mixtures thereof.

13. The method of claim 12, wherein said conditioning agent is silicone.

14. The method of claim 13, wherein said silicone is selected from the group consisting of siloxanes, silicone gums, aminosilicones, terminal aminosilicones, alkyl siloxane polymers, cationic organopolysiloxanes, and mixtures thereof.

15. The method of claim 14, wherein said silicone is terminal aminosilicone.

16. The method of claim 1, wherein said first benefit agent is conditioning agent and said second benefit agent is perfume.

17. The method of claim 1, wherein said hydrophobic coating further comprises viscosity modifier, surfactant, or mixtures thereof.

* * * * *